(12) United States Patent
Nakashima et al.

(10) Patent No.: US 9,452,036 B2
(45) Date of Patent: Sep. 27, 2016

(54) DENTAL ULTRASONIC DRUG DELIVERY SYSTEM AND DENTAL ULTRASONIC DRUG DELIVERY METHOD

(75) Inventors: Misako Nakashima, Obu (JP); Katsuro Tachibana, Fukuoka (JP)

(73) Assignees: National Center for Geriatrics and Gerontology, Obu-Schi, Aichi (JP); Fukuoka University, Fukuoka-Shi, Fukuoka (JP)

( * ) Notice: Subject to any disclaimer, the term of this patent is extended or adjusted under 35 U.S.C. 154(b) by 190 days.

(21) Appl. No.: 13/516,678

(22) PCT Filed: Dec. 16, 2010

(86) PCT No.: PCT/JP2010/007315
§ 371 (c)(1),
(2), (4) Date: Jun. 15, 2012

(87) PCT Pub. No.: WO2011/074268
PCT Pub. Date: Jun. 23, 2011

(65) Prior Publication Data
US 2012/0270177 A1 Oct. 25, 2012

(30) Foreign Application Priority Data
Dec. 16, 2009 (JP) ................................ 2009-285068

(51) Int. Cl.
*A61C 1/07* (2006.01)
*A61C 17/02* (2006.01)
(Continued)

(52) U.S. Cl.
CPC ........... *A61C 17/0202* (2013.01); *A61C 17/20* (2013.01); *A61C 5/02* (2013.01)

(58) Field of Classification Search
CPC ........ A61C 17/20; A61C 1/07; A61C 17/00; B08B 3/12

USPC .................................. 433/80–90, 119, 224
See application file for complete search history.

(56) References Cited

U.S. PATENT DOCUMENTS 4,116,239 A * 9/1978 Ewen ..................... 128/200.16
5,125,837 A * 6/1992 Warrin et al. .................. 433/98
(Continued)

FOREIGN PATENT DOCUMENTS

| JP | 05-155745 | 6/1993 |
| JP | 05-155746 | 6/1993 |

(Continued)

OTHER PUBLICATIONS

English language machine translation of JP 2009-189753, Aug. 27, 2009.*

(Continued)

*Primary Examiner* — Yogesh Patel
(74) *Attorney, Agent, or Firm* — Knobbe Martens Olson & Bear, LLP

(57) ABSTRACT

A dental ultrasonic drug delivery system capable of accurately cleaning the inside of root canals and killing bacteria in dentin tubules is provided. The dental ultrasonic drug delivery system delivers a drug to a target using an ultrasonic delivery device 800. The drug is delivered in a mixed state with nanobubbles. A dental therapeutic probe for applying ultrasound is attached to the ultrasonic delivery device 800. The dental therapeutic probe is selected from: (1) a root canal insertion probe 100 which is configured to be inserted into a root canal and causes ultrasound to propagate in the root canal; (2) a dental caries therapeutic probe which causes ultrasound to propagate in a dental caries portion; (3) a periodontal disease therapeutic probe which applies ultrasound to a periodontal disease portion; and (4) a hyperesthesia therapeutic probe which applies ultrasound to hyperesthesia portion.

4 Claims, 32 Drawing Sheets

(51) Int. Cl.
   *A61C 17/20*   (2006.01)
   *A61C 5/02*   (2006.01)

(56) References Cited

U.S. PATENT DOCUMENTS

| | | | | |
|---|---|---|---|---|
| 5,419,703 | A | * | 5/1995 | Warrin ............... A61C 1/0084 433/216 |
| 5,639,238 | A | * | 6/1997 | Fishburne, Jr. ........ A61H 13/00 433/215 |
| 5,853,290 | A | | 12/1998 | Winston |
| 6,413,220 | B1 | * | 7/2002 | Rose .................... A61C 19/043 433/72 |
| 7,296,318 | B2 | * | 11/2007 | Mourad ............ A46B 15/0002 15/22.1 |
| 2004/0126732 | A1 | * | 7/2004 | Nusstein ........................ 433/81 |
| 2004/0258760 | A1 | | 12/2004 | Wheatley et al. |
| 2006/0019220 | A1 | * | 1/2006 | Loebel .................. A61C 1/088 433/215 |
| 2006/0134016 | A1 | | 6/2006 | Tachibana et al. |
| 2006/0252010 | A1 | * | 11/2006 | Sunnen ............... A61C 19/063 433/215 |
| 2006/0257819 | A1 | * | 11/2006 | Johnson ......................... 433/86 |
| 2007/0148615 | A1 | | 6/2007 | Pond |
| 2008/0044789 | A1 | | 2/2008 | Johnson |
| 2008/0311540 | A1 | * | 12/2008 | Gottenbos ............. A61C 17/20 433/86 |
| 2008/0319377 | A1 | * | 12/2008 | Keenan ........................... 604/24 |
| 2009/0042163 | A1 | | 2/2009 | Johnson |

| | | | |
|---|---|---|---|
| 2009/0117177 | A1 | 5/2009 | Rapoport et al. |
| 2009/0162810 | A1 | 6/2009 | Werner et al. |
| 2011/0111365 | A1 | 5/2011 | Gharib et al. |
| 2012/0276497 | A1 | 11/2012 | Gharib et al. |

FOREIGN PATENT DOCUMENTS

| | | |
|---|---|---|
| JP | 11-240816 | 9/1999 |
| JP | 2004-182728 A2 | 7/2004 |
| JP | 2004-313659 A | 11/2004 |
| JP | 2006-006570 | 1/2006 |
| JP | 2006-167330 | 6/2006 |
| JP | 2007-229110 | 9/2007 |
| JP | 2008-100956 | 5/2008 |
| JP | 2008-542293 A | 11/2008 |
| JP | 2009-045455 A | 3/2009 |
| JP | 2009-153825 | 7/2009 |
| JP | 2009-165449 | 7/2009 |
| JP | 2009-165499 | 7/2009 |
| JP | 2009-189753 | 8/2009 |
| WO | WO 2004/049964 A2 | 6/2004 |
| WO | WO 2006/001224 A1 | 1/2006 |
| WO | WO 2007/117010 A1 | 10/2007 |
| WO | 2009/137815 A1 | 11/2009 |

OTHER PUBLICATIONS

Extended European Search Report dated Apr. 29, 2013, for European Patent Application No. EP 10 83 7299.

* cited by examiner

DENTAL ULTRASONIC DRUG DELIVERY SYSTEM AND DENTAL ULTRASONIC DRUG DELIVERY METHOD

TECHNICAL FIELD

The present disclosure relates to dental ultrasonic drug delivery systems and methods for delivering a drug into a target site such as a periapical lesion or a dental caries portion using a dental therapeutic probe for emitting ultrasound.

BACKGROUND ART

Dental caries is one of the two major dental diseases including a periodontal disease, and about a half of tooth loss is due to dental caries. Similarly to a cold, dental caries is commonly seen in any generation. Especially children readily suffer from dental caries for several years after tooth eruption, showing low calcification, and dental caries is often seen in people under 20. Dental pulp, a so-called nerve of a tooth, has functions of blocking external stimulus by tooth (dentin) formation potential and inhibiting development of dental caries and tooth fracture by sense. Dental pulp also has an important function in tooth survival by metabolic and immune systems.

With a current pulpectomy technique, complete pulpectomy and root canal filling are almost impossible, and abnormality occurs in apical areas (periapical periodontitis) in a later stage, leading to the necessity of an infected root canal treatment in many cases. In such cases, a single chair time is longer than that in a dental caries treatment, and a long-term treatment is often needed. It is also possible that symptoms such as drainage from the apical foramen or pain are not improved, which leads to a tooth loss by tooth extraction. Tooth pain causes severe difficulties in daily life, and reduces social productivity. As dental caries grows to dental pulp and further to bone in the apical area to finally cause tooth extraction, mental and economic burdens of patients increase, and declined functions of mouth and occlusion cause motor dysfunction, autonomic imbalance, and problems in pronunciation and aesthetics.

In conventional dental caries treatments, it is necessary to physically completely remove dental caries (softened dentin) in order to completely kill bacteria which have invaded deep parts of dentin tubules. This removal increases the possibility of excessive loss of dentin, leading to exposure of dental pulp.

There is also a root canal treatment known as the treatment of removing a portion suffering from dental caries and cleaning and disinfecting the inside of a root canal. In the root canal treatment, a portion suffering from dental caries is first removed, and then enamel and dentin are removed as necessary in order to easily perform the root canal treatment. Next, after the depth of the root canal has been precisely measured with, for example, the sense of fingers, X-ray photographs, or an electronic root canal length measurement, dental pulp or dentin infected by bacteria is removed with a tool such as a reamer or a file. Thereafter, a predetermined drug is placed in the root canal from which dental pulp has been removed, and the root canal is irrigated, cleaned, and disinfected with a tool such as a broach. Lastly, the root canal is filled with gutta-percha, thus finishing the root canal treatment.

The root canal treatment is classified into a pulpectomy treatment and an infected root canal treatment. If dental caries is deep enough to reach dental pulp, the pulpectomy treatment is generally employed. The pulpectomy treatment is a removal of dental pulp inside a tooth. Dental pulp which is or might be infected is thoroughly removed by the pulpectomy treatment. Thus, it is possible to prevent inflammation from reaching periodontal tissue, and a tooth affected by caries is made harmless to periodontal tissue, thereby recovering chewing ability.

An infected root canal refers to a state in which dental caries develops to dental pulp to cause necrosis of the dental pulp due to infection or a state in which insufficient filling of the root canal causes infection of the inside of the root canal. The infected root canal treatment is employed in these cases. In a severely infected root canal, an apical periodontal cyst or a fistula (a passageway through which pus accumulated around teeth is drained) is created. In the case of the infected root canal, it is necessary to clean and disinfect the inside of the root canal before filling the root canal. If the root canal was insufficiently filled with a root canal filler in the past, the root canal filler is temporarily removed so that the inside of the root canal is cleaned and disinfected again, and then the root canal is filled to the root apex.

However, it is difficult to observe the structure directly in the root canal, and the shape of the root canal is complex such that the root canal is curved or blocked and has a large number of accessory canals, lateral branches, or the like. Thus, it is very difficult to remove bacteria completely in the root canal. In addition, if the root canal is filled with a filler or covered with a crown with bacteria being left in the root canal, the bacteria will proliferate in the root canal later in some cases, leading to the necessity of an additional root canal treatment. In a case where an additional root canal treatment is required later, the filling or the crown used in the previous treatment needs to be replaced with new one, and further, the possibility of tooth extraction might arise. If the treatment is excessively localized on removal of residual bacteria in the root canal, dentin can be excessively removed, which lead to better the patients' quality of life (QOL). Since the shape of a root canal is complex as described above, the root canal treatment (treatment of dental nerves and roots) is very difficult.

Patent Document 1 describes a system for irrigation of a tooth root canal using ultrasonic energy. The system for irrigation of a tooth root canal includes an injection tube having a flexible distal end configured to be inserted into a root canal. This injection tube is inserted into the root canal so that a fluid having ultrasonic energy superimposed thereon is forced into the root canal, thus performing irrigation.

In the system for irrigation of a tooth root canal described in Patent Document 1, however, the fluid having ultrasonic energy superimposed thereof is merely released to the apical area of the root canal, and it is difficult to irrigate minute portions of the root canal with a complex shape.

Patent Document 2 describes a tooth root canal treatment system including a motor for rotatably driving a root canal drill. Driving of this motor is controlled in the following manner. In inserting the root canal drill into a root canal with the motor rotated in the reverse direction to the rotation direction of the root canal drill for cutting the root canal, rotation in the reverse direction of the root canal drill is maintained until an electronic root-canal-length measurement detects that the distal end of the root canal drill reaches a predetermined reference position. When the electronic root-canal-length measurement detects that the distal end of the root canal drill has reached the reference position, the rotation in the reverse direction of the root canal drill is stopped.

In the tooth root canal treatment system described in Patent Document 2, the root canal drill can be rotated in the reverse direction to the direction of rotation for cutting the root canal. In this system, after the root canal has been drilled and enlarged by rotating the root canal drill in the positive direction, a drug solution is injected into the root canal. Then, the root canal drill is rotated in the reverse direction and inserted into the root canal so that positive rotation of the root canal drill causes small cuttings produced by drilling to be ejected to the proximal end (upstream) of the root canal drill. Accordingly, the above-mentioned insertion with the reverse rotation pushes the drug solution toward the distal end of the root canal drill.

In the tooth root canal treatment system described in Patent Document 2, however, the root canal drill might excessively drill and enlarge the root canal. In addition, although the drug solution is sufficiently injected into the distal end of the root canal drill, the lateral branches of the root canal are not sufficiently taken into consideration, and thus, it is difficult to irrigate minute portions of the complex root canal.

Patent Document 3 describes a dental therapeutic system in which a liquid supply nozzle for supplying a drug solution (a therapeutic solution) or the like and a suction nozzle are inserted into a root canal with the tips thereof positioned at different locations and a drug solution is injected so that the drug solution fully permeates the root canal. If the liquid supply nozzle and the suction nozzle are positioned such that one of these nozzles is located at a portion deeper than the other in the cavity, the treatment solution reaches at least the deep portion in the cavity. Accordingly, a target area is efficiently irrigated.

In the dental therapeutic system described in Patent Document 3, however, since the tip apertures of the liquid supply nozzle and the suction nozzle for the drug solution face the apical area of the root canal, even if the apical area can be irrigated, the other areas are insufficiently irrigated.

Periodontal disease (periodontal disorder) is inflammation of periodontal tissue which supports teeth. Periodontal tissue is a general term including cementum, gingiva, alveolar bone, and periodontium. Periodontal disease is a disease caused by infection with periodontal disease bacteria from so-called gingival sulci (periodontal pockets) between teeth and gingivae. The periodontal disease is broadly classified into gingivitis with no alveolar bone resorption and periodontitis with alveolar bone resorption. In either case, induced inflammation tends to enlarge periodontal pockets.

Oral rinses, dentifrices, and antibiotics, for example, are known as conventional therapeutic drugs for periodontal diseases. Conventional therapeutic methods include brushing with tooth brushes, and dental calculus removal and irrigation performed in dental clinics. However, the use of dentifrices has the possibility of insufficient cleaning of periodontal pockets if brushing is insufficient. In the case of using oral rinses, although the oral rinses spread in the mouth, the drug solution is not effective in some areas such as periodontal pockets. In the case of antibiotics, arrival of medicinal ingredients at inflammed areas such as gingivae takes too much time after administration, and the antibiotics are not effective against all the periodontal disease bacteria. Patent Document 4 proposes an embrocation liquid for periodontal diseases using shellac as a base material in a tooth coating composition. However, disadvantageously, this embrocation liquid cannot be used in periodontal pockets.

Next, hyperesthesia is a disease in which advanced periodontal disease causes transient pain when the surface of exposed dentin is subjected to cold air, cold water, or tactil stimuli, for example. Exposure of dentin is caused by enamel disappearing or gingival retraction, for example. In the exposed dentin, mechanical wearing or elution of lime due to action of acid or the like forms openings in dentin tubules through which physicochemical stimuli are transmitted to dental pulp to stimulate nerves and cause pain.

For hyperesthesia therapy, there is a technique of filling openings in dentin tubules. For example, Patent Document 5 describes a technique in which a tooth is subjected to a treatment using a water-soluble aluminium compound and fluoride. Patent Document 6 shows a technique in which a tooth is subjected to a treatment using a water-soluble aluminium compound, fluoride, and water-soluble calcium. However, disadvantageously, these techniques cannot have drugs easily permeate dentin tubules, and insufficiently fill the dentin tubules.

CITATION LIST

Patent Document

[Patent Document 1] Japanese Patent Publication No. 2009-045455 (page 2, FIG. 1)

[Patent Document 2] Japanese Patent Publication No. 2007-229110 (page 2)

[Patent Document 3] Japanese Patent Publication No. 2004-313659 (page 2, FIG. 1)

[Patent Document 4] Japanese Patent Publication No. H11-240816

[Patent Document 5] Japanese Patent Publication No. H05-155745

[Patent Document 6] Japanese Patent Publication No. H05-155746

SUMMARY OF THE INVENTION

Technical Problem

As described above, the inside of a root canal has a complex shape, and thus, a root canal treatment is very difficult to conduct. However, without an appropriate root canal treatment, periapical periodontitis will arise later, resulting in suppuration of the apical area of the root. It is also difficult for drugs to permeate periodontal pockets and dentin tubules, and adequate treatments for periodontal disease and hyperesthesia are needed. It is therefore an object of the present disclosure to provide a dental ultrasonic drug delivery system and a dental ultrasonic drug delivery method capable of accurately cleaning the inside of root canals with complex shapes, and also capable of filling openings in dentin tubules by allowing a drug to permeate dentin tubules and of killing bacteria in the dentin tubules.

Solution to the Problem

A dental ultrasonic drug delivery system in a first aspect of the present disclosure is a dental ultrasonic drug delivery system for delivering a drug to a target using a dental therapeutic probe for applying ultrasound. The drug is delivered in a mixed state with nanobubbles. The dental therapeutic probe is selected from: (1) a root canal insertion probe which is configured to be inserted into a root canal and causes ultrasound to propagate in the root canal; (2) a dental caries therapeutic probe which causes ultrasound to propagate in a dental caries portion; (3) a periodontal disease therapeutic probe which applies ultrasound to a periodontal disease portion; and (4) a hyperesthesia therapeutic probe which applies ultrasound to hyperesthesia portion.

The root canal insertion probe preferably causes ultrasound to propagate toward an apical area or a lateral branch of the root canal.

Preferably, the periodontal disease therapeutic probe has a tubular body, includes a periodontal pocket irradiation part which is located at a distal end of the tubular body and causes ultrasound to propagate to a periodontal pocket, and also includes a drug delivery tube which is located inside the tubular body and delivers the drug, in the mixed state with nanobubbles, to the periodontal pocket.

Preferably, the hyperesthesia therapeutic probe includes a wedge-shaped defect portion pad formed by modeling an impression of a wedge-shaped defect portion of tooth enamel, and causes ultrasound to propagate to the wedge-shaped defect portion through the wedge-shaped defect portion pad.

The target preferably may include at least one of a periapical lesion of an apical area, an accessory canal, a dentin tubule, a periodontal pocket, or a wedge-shaped defect portion of enamel.

Each of the nanobubbles preferably has a diameter of 10 nm to 500 nm, both inclusive.

A frequency of ultrasound with which the drug is delivered is preferably in the range from 800 KHz to 2 MHz, both inclusive.

The drug may include at least one of a sodium hypochlorite solution, a hydrogen peroxide solution, formalin cresol, formalin guaiacol, phenol, phenol camphor, parachlorophenol camphor, cresatin, guaiacol, cresol, iodine tincture, an EDTA product, a calcium hydroxide solution, a tetracycline hydrochloride solution, ampicillin, imipenem, panipenem, vancomycin, chloramphenicol PBSS, PBSC, ofloxacin, levofloxacin, metronidazole, cefaclor, ciprofloxacin, imidazole, a cathepsin K inhibitor, BMPs, or bFGF.

The drug for use in periodontal disease therapy may include at least one of isopropylmethyl phenol, thymol, clove oil, dipotassium glycyrrhizinate, allantoin, hinokitiol, cetylpyridinium chloride, panthenol, tocopherol acetate, sodium lauroyl sarcosine, tranexamic acid, ε-aminocaproic acid, bisphosphonate, tetracycline, presteron, minocycline, doxycycline, ofloxacin, levofloxacin, metronidazole, amoxicillin, a cathepsin K inhibitor, chlorhexidine, hypochlorous acid, BMPs, or bFGF.

The drug for use in hyperesthesia therapy may include at least one of oxalic acid, a diamine silver fluoride product, copal resin, sodium fluoride, zinc chloride, a water-soluble aluminium compound, water-soluble calcium, BMPs, or bFGF.

A dental ultrasonic drug delivery method in a second aspect of the present disclosure is a dental ultrasonic drug delivery method for delivering a drug by applying ultrasound to a tooth or periodontal tissue of an animal except for a human. In this method, the drug is delivered, in a mixed state with nanobubbles, to the tooth or the periodontal tissue.

Each of the nanobubbles preferably has a diameter of 10 nm to 500 nm, both inclusive.

The frequency of ultrasound with which the drug is delivered is preferably in the range from 800 KHz to 2 MHz, both inclusive.

Advantages of the Invention

According to the present disclosure, nanobubbles enter the complex structure of a root canal, and ultrasound irradiation causes a cavitation effect to allow a drug to permeate the complex structure of the root canal, thereby accurately cleaning the inside of the root canal. In addition, the drug also permeates a periodontal pocket, thereby accurately cleaning the inside of the pocket, cementum, and dentin. Since nanobubbles enter dentin tubules and ultrasound irradiation causes a cavitation effect to allow a drug to permeate the dentin tubules, the inside of the dentin tubules can be accurately cleaned. In addition, the permeation of the drug in the dentin tubules provides appropriate hyperesthesia therapy. According to the present disclosure, bacteria in root canals and dentin tubules can be accurately sterilized in a short time. Thus, excessive tooth removal can be prevented, and the number of visits to hospital and the chair time can be reduced, thereby providing high-quality effective dental care.

DESCRIPTION OF EMBODIMENTS (First Embodiment)

Embodiments of the present disclosure will be described hereinafter with reference to the drawings. In a dental ultrasonic drug delivery system 900 according to an embodiment of the present disclosure, a drug in a mixture state with nanobubbles is delivered into a target, and the target is irradiated with ultrasound by using an ultrasonic delivery device 800.

Figure 1:
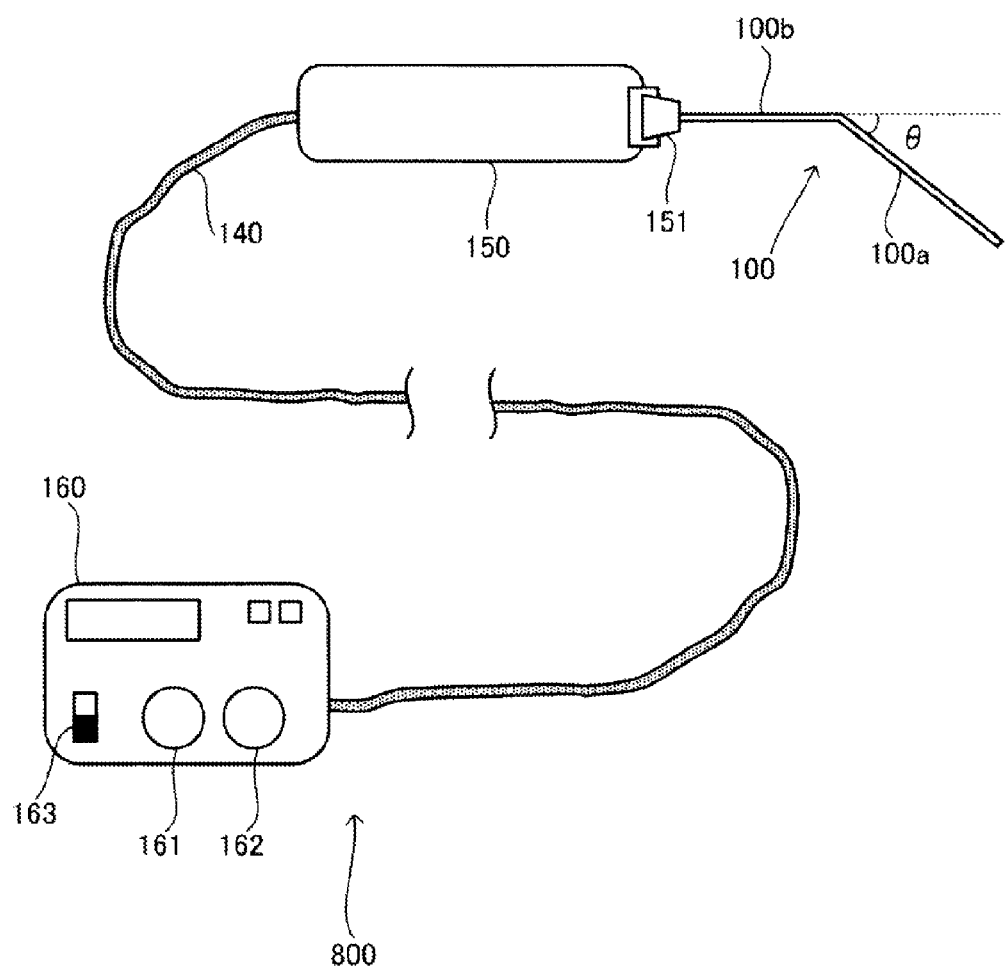
FIG. 1 is a view schematically illustrating a perspective view of an ultrasonic delivery device provided with a root canal insertion probe.

As illustrated in FIG. 1, the ultrasonic delivery device 800 includes: a probe body 150; a root canal insertion probe 100 provided in the probe body 150; and a manipulation section 160. The connection unit 140 electrically connects the manipulation section 160 and the probe body 150. The manipulation section 160 includes: a frequency adjustment unit 161 for adjusting the frequency of ultrasound; and an intensity adjustment unit 162 for adjusting the intensity of ultrasound. The manipulation section 160 includes a power supply 163 for turning on/off a power supply to the ultrasonic delivery device 800.

To hold the insert probe body 150 and easily insert the distal end of the root canal insertion probe 100 into a root canal, the root canal insertion probe 100 includes a distal probe 100a and a proximal probe 100b, and is bent to form an approximate L shape. The angle θ of the approximate L shape of the root canal insertion probe 100 is not specifically limited as long as the root canal insertion probe 100 is easily inserted into a root canal. For example, the angel θ can be 30-80°, and preferably 60°. The size of the root canal insertion probe 100 is not specifically limited as long as the root canal insertion probe 100 is inserted into the root canal. For example, the root canal insertion probe 100 is circular in cross section, and has a diameter of 0.3 mm to 1.2 mm, preferably 0.4 mm to 0.8 mm, and more preferably 0.5 mm The length of the root canal insertion probe 100 is not specifically limited. For example, the length of the proximal probe 100b is 1.0 cm to 1.6 cm, and the length of the distal probe 100a is 1.5 cm to 3.0 cm. The root canal insertion probe 100 is preferably made of a lightweight material which is resistant to corrosion, and may be made of stainless used steel (SUS).

The probe body 150 is provided with a fixing screw 151. The root canal insertion probe 100 is detachably fixed to the probe body 150 with the fixing screw 151 interposed therebetween. Specifically, the proximal end of the root canal insertion probe 100 has an external thread, which engages with an internal thread formed on the fixing screw 151. The root canal insertion probe 100 may be removed so that the root canal insertion probe 100 is replaced with a dental caries therapeutic probe 130, which will be described later. In this manner, the probe body 150 can be commonly used so as to make it possible to selectively replace only the probe depending on the purpose of treatment. The root canal insertion probe 100 may be integrated with the probe body 150.

Figure 2A:
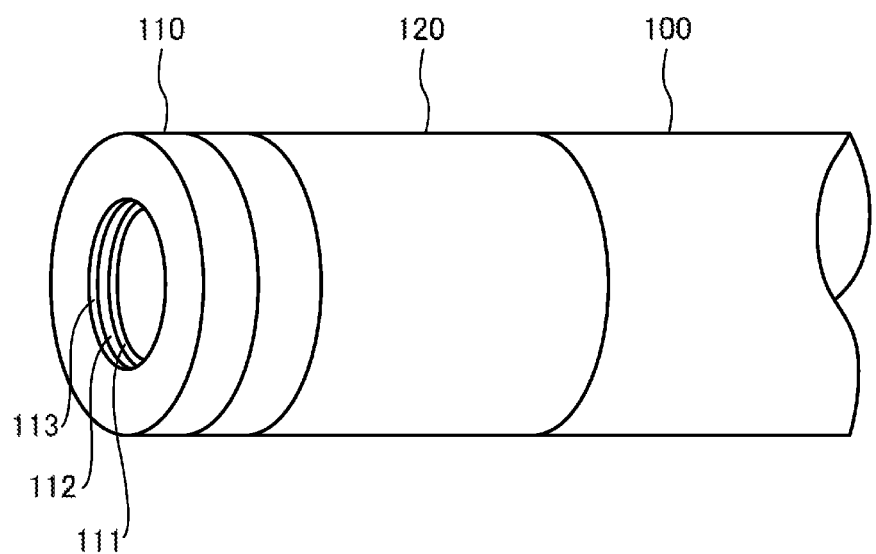
FIG. 2A is a view schematically illustrating an apical area irradiation part and a lateral branch irradiation part of a root canal insertion probe.
Figure 2B:
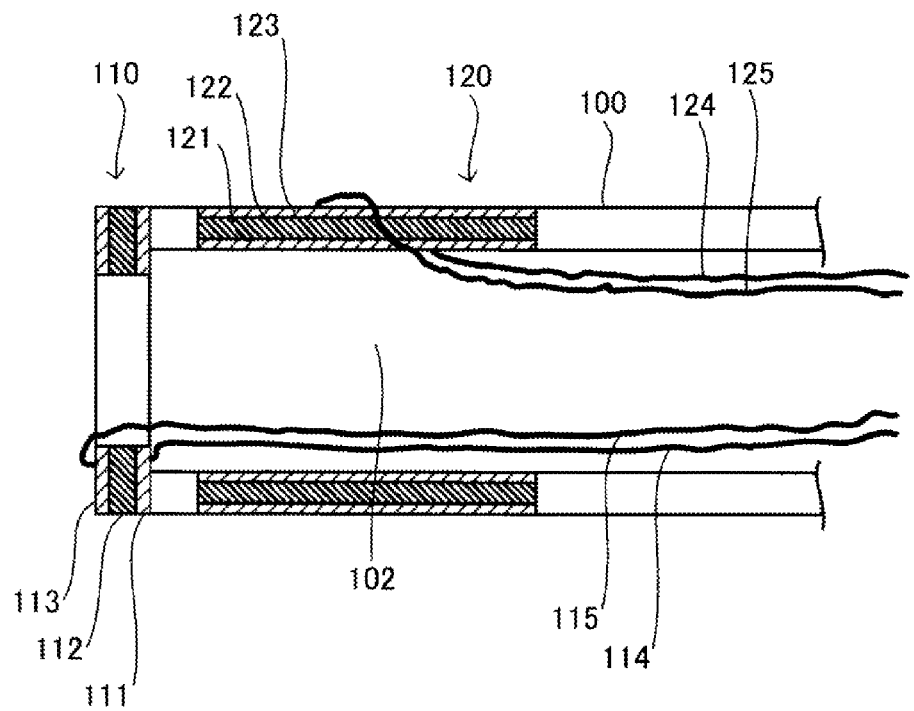
FIG. 2B is a cross-sectional view illustrating the apical area irradiation part and the lateral branch irradiation part of the root canal insertion probe.

FIG. 2A is a view schematically illustrating an apical area irradiation part and a lateral branch irradiation part of the root canal insertion probe. FIG. 2B is a cross-sectional view illustrating the apical area irradiation part and the lateral branch irradiation part of the root canal insertion probe.

As illustrated in FIG. 2A, the root canal insertion probe 100 includes: an apical area irradiation part 110 for irradiating an apical area of a root canal with ultrasound; and a lateral branch irradiation part 120 for irradiating a lateral branch of the root canal with ultrasound. The apical area irradiation part 110 is located at the distal end of the root canal insertion probe 100, and applies ultrasound in the longitudinal direction of the probe. The lateral branch irradiation part 120 is located slightly at the rearward of the distal end of the root canal insertion probe 100, and applies ultrasound in the transverse direction of the probe.

As illustrated in FIGS. 2A and 2B, the apical area irradiation part 110 including an ultrasonic transducer constituted by: a cylindrical piezoelectric element 112; a tubular inner electrode 111 located on the inner side of the piezoelectric element 112; and a cylindrical outer electrode 113 located on the outer side of the piezoelectric element 112.

The surface of the inner electrode 111 is coated with an insulator, and thereby, is electrically insulated from the outside. The outer electrode 113 is electrically exposed to the outside. As illustrated in FIG. 2B, the inner electrode 111 and the outer electrode 113 are electrically connected to lead wires 114 and 115, respectively, and the lead wires 114 and 115 are guided to outside the root canal insertion probe 100.

In addition, as illustrated in FIG. 2B, the lateral branch irradiation part 120 includes an ultrasonic transducer constituted by: a cylindrical piezoelectric element 122; a tubular inner electrode 121 located on the inner side of the piezoelectric element 122; and a cylindrical outer electrode 123 located on the outer side of the piezoelectric element 122.

The surface of the inner electrode 121 is coated with an insulator, and thereby, is electrically insulated from the outside. The outer electrode 123 is electrically exposed to the outside. The inner electrode 121 and the outer electrode 123 are electrically connected to lead wires lead wires 124 and 125, and the lead wires 124 and 125 are guided to outside the root canal insertion probe 100.

As will be described later, the frequency of ultrasound is not specifically limited as long as cavitation occurs to allow a drug to permeate the complex structure of a root canal. For example, the frequency of ultrasound is 100 KHz to 10 MHz, preferably 800 KHz to 2 MHz, and particularly preferably about 1 MHz. The irradiation time of ultrasound is not specifically limited, and is 10 seconds to 10 minutes, for example, preferably 20 seconds to 3 minutes, and particularly preferably 2 minutes.

The intensity of ultrasound is not specifically limited as long as cavitation occurs in a preferable manner without damage to dental tissue of, for example, a root canal. The intensity of ultrasound is 1-30 W/cm$^2$, for example, preferably 10-25 W/cm$^2$, and particularly preferably about 20 W/cm$^2$.

Figure 3:
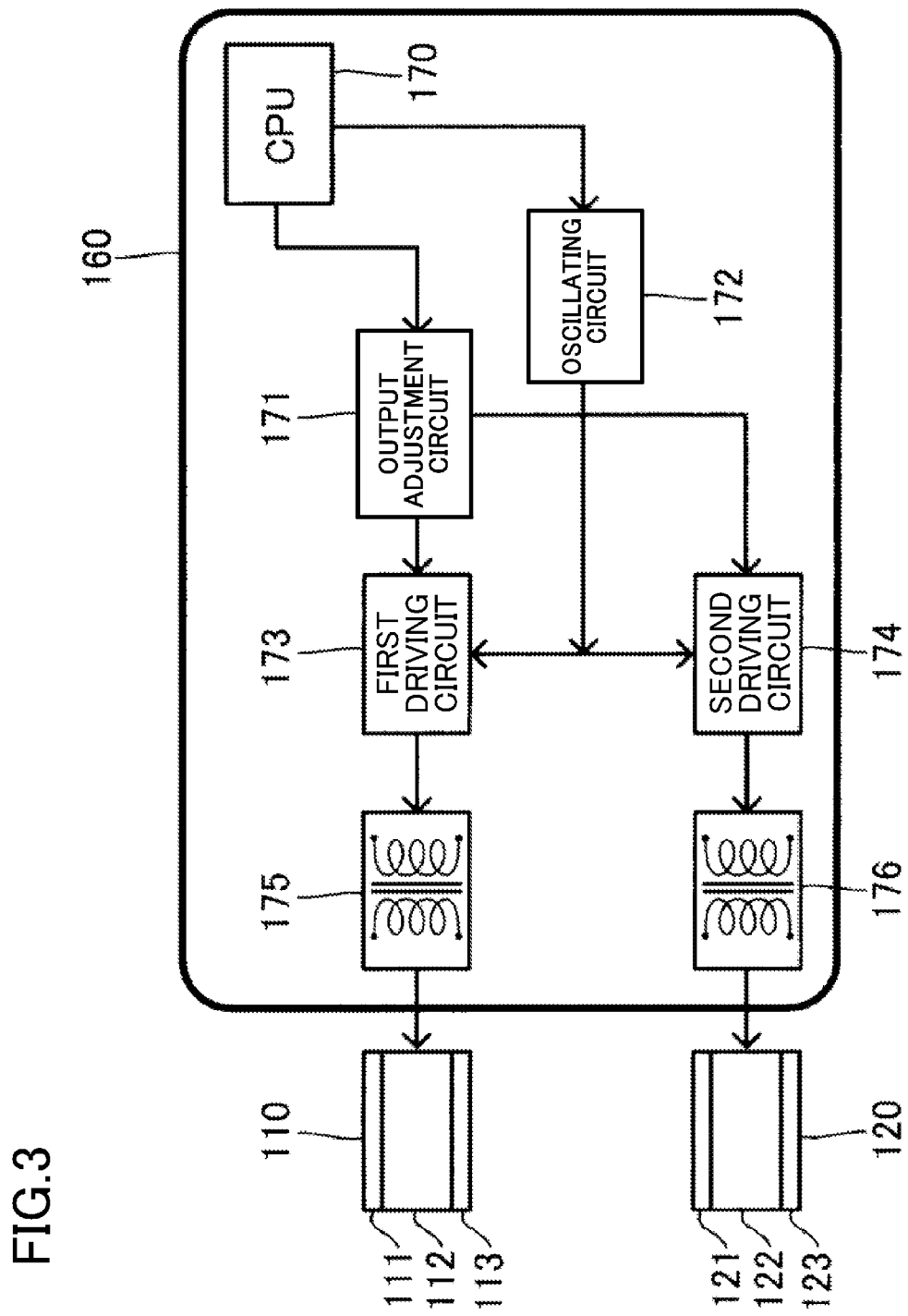
FIG. 3 is a circuit diagram showing a signal or a voltage applied to the apical area irradiation part and the lateral branch irradiation part.

FIG. 3 is a circuit diagram showing a signal or a voltage applied to the apical area irradiation part 110 and the lateral branch irradiation part 120.

An ultrasound control block for controlling the apical area irradiation part 110 and the lateral branch irradiation part 120 includes a CPU 170, an output adjustment circuit 171, an oscillating circuit 172, a first driving circuit 173, a second driving circuit 174, a first isolation transformer 175, and a second isolation transformer 176.

Although not shown in FIG. 3, the lead wires 114 and 115 derived from the inner electrode 111 and the outer electrode 113 illustrated in FIG. 2B are respectively connected to one terminal and the other terminal of a secondary winding of the first isolation transformer 175. The lead wires 124 and 125 derived from the inner electrode 121 and the outer electrode 123 illustrated in FIG. 2B are respectively connected to one terminal and the other terminal of a secondary winding of the second isolation transformer 176.

The output adjustment circuit 171 indicates, to the first driving circuit 173 and the second driving circuit 174, the amplitudes of driving signals to be sent to the ultrasonic transducers in association with the ultrasonic transducer of the apical area irradiation part 110 and the ultrasonic transducer of the lateral branch irradiation part 120. The output adjustment circuit 171 individually and arbitrarily sets the intensity of ultrasonic vibration to be applied to a load within an allowable range for each of the ultrasonic transducers. Specifically, the output adjustment circuit 171 indicates the amplitude based on an instruction given from the outside.

The oscillating circuit 172 generates an alternating current (AC) signal with a drive frequency associated with each of the ultrasonic transducers, and provides the generated AC signal to an associated one of the first driving circuit 173 or the second driving circuit 174.

The first driving circuit 173 amplifies an AC signal having a drive frequency previously set with respect to the ultrasonic transducer of the apical area irradiation part 110 and sent from the oscillating circuit 172 to an amplitude indicated by the output adjustment circuit 171, and supplies the amplified driving signal to the ultrasonic transducer of the apical area irradiation part 110, thereby driving the ultrasonic transducer.

The second driving circuit 174 amplifies an AC signal having a drive frequency previously set with respect to the ultrasonic transducer of the lateral branch irradiation part 120 and sent from the oscillating circuit 172 to an amplitude indicated by the output adjustment circuit 171, and supplies the amplified driving signal to the ultrasonic transducer of the lateral branch irradiation part 120, thereby driving the ultrasonic transducer.

The shapes, e.g., diameters, of the ultrasonic transducer of the apical area irradiation part 110 and the ultrasonic transducer of the lateral branch irradiation part 120 may be different from each other or may be the same. The drive frequencies of the ultrasonic transducers of the apical area irradiation part 110 and the lateral branch irradiation part 120 may also be different from each other or may be the same.

The CPU 170 functions as a control center which controls operation of the ultrasound control block, and has functions of, for example, a microcomputer having resources, such as a processing unit, a storage unit, and an input/output unit, necessary for computers controlling processing based on programs.

Based on a control logic (a program) previously held inside, the CPU 170 provides instructions to components, including the oscillating circuit 172 and the output adjustment circuit 171, which need to be controlled by the ultrasound control block, and manages and controls all the operations necessary for controlling driving of the ultrasonic transducers.

The ultrasonic transducer of the apical area irradiation part 110 and the ultrasonic transducer of the lateral branch irradiation part 120 are driven at the same time, or are selectively driven, based on a drive command from the outside.

Specifically, when a drive instruction for the ultrasonic transducer of the apical area irradiation part 110 is issued, an AC signal with a drive frequency previously set in association with the ultrasonic transducer of the apical area irradiation part 110 is generated by the oscillating circuit 172, and this AC signal is sent to the first driving circuit 173. The intensity of vibration of the ultrasonic transducer of the apical area irradiation part 110 sent from the outside, i.e., a voltage amplitude (an amplification factor of an AC signal output from the oscillating circuit 172) of a driving signal supplied to the ultrasonic transducer, is transmitted from the output adjustment circuit 171 to the first driving circuit 173.

In the manner described above, the AC signal with a drive frequency sent from the oscillating circuit 172 is amplified in the first driving circuit 173 with an amplification factor given from the output adjustment circuit 171, thereby generating a driving signal. This driving signal is supplied to the ultrasonic transducer of the apical area irradiation part 110, thereby driving the ultrasonic transducer of the apical area irradiation part 110.

A drug for sterilizing a target is delivered in a mixture state with nanobubbles. The target is not specifically limited, and is a tooth or periodontal tissue, for example, and particularly periapical lesions of apical areas, dentin tubules, accessory canals, periodontal pockets, and wedge-shaped defect portions of enamel.

Figure 4A:
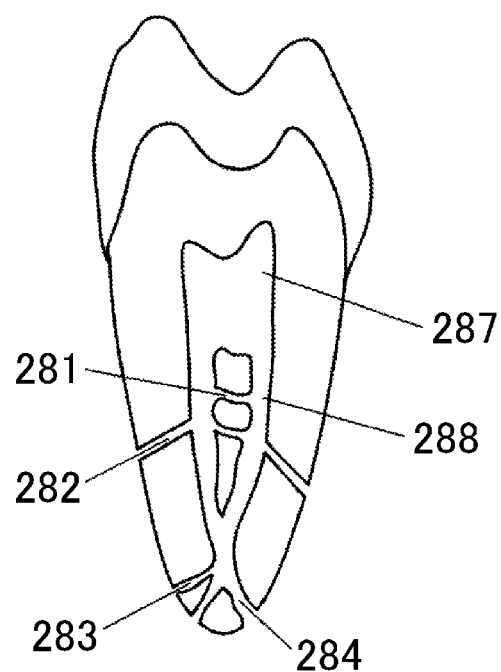
FIG. 4A is a view illustrating a lateral branch in an anatomical structure of an accessory canal.
Figure 4B:
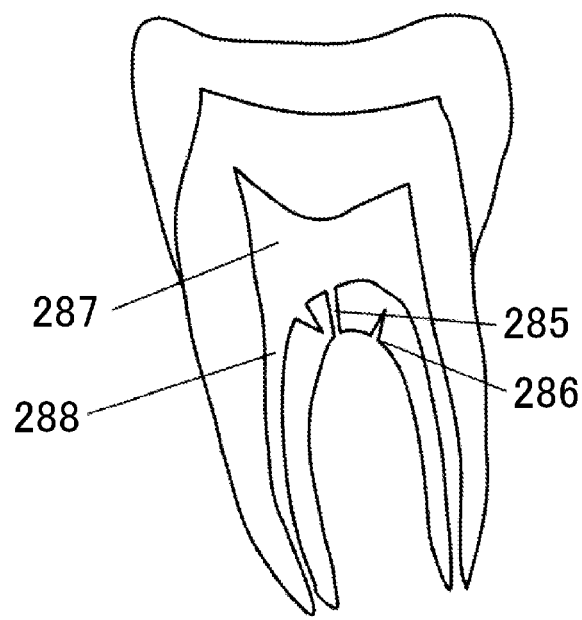
FIG. 4B is a view illustrating a medullary tube in an anatomical structure of an accessory canal.

FIG. 4A is a view illustrating a lateral branch in an anatomical structure of an accessory canal. FIG. 4B is a view illustrating a medullary tube 285 in an anatomical structure of an accessory canal. The dental pulp includes coronal pulp 287 and root pulp 288 located under the coronal pulp 287. The accessory canal is a general term including various tubules branching off from a main root canal. In addition to lateral branches, the accessory canal includes: an apical ramification 283 formed by a branch of the main root canal in an apical area; and a medullary tube 285 observed in a furcation area of a molar tooth. As illustrated in FIG. 4A, lateral branches are tubules branching off from a main root canal and observed from the center to the apex of a tooth root. The lateral branches include a canal external lateral branch 282 and a canal internal lateral branch 281. The canal external lateral branch 282 extends substantially perpendicularly or in a slanting direction from the main root canal, opens at the side surface of the tooth root except for an apical foramen 284, and communicates with periodontium tissue. On the other hand, the canal internal lateral branch 281 is, for example, a lateral branch coupling root canals or the like in a furcated root canal at the buccal and lingual side such as an upper premolar tooth. The apical ramification 283 often appears in the mesiobuccal roots of the second premolar tooth and the first and second molar teeth in the upper jaw, and in the mesial roots of the first and second molar teeth in the lower jaw. As illustrated in FIG. 4B, the medullary tube 285 is a tubule connecting the floor of pulp chamber of a molar tooth and a periodontium. A furcation area includes one to several medullary tubes 285. The medullary tubes 285 include: a so-called complete medullary tube through which a coronal pulp cavity and periodontium tissue directly communicate with each other; and a cul-de-sac 286 through which a coronal pulp cavity and periodontium tissue does not directly communicate with each other and which is partially closed at one end as a blind end.

The mixture ratio of a drug and nanobubbles is not specifically limited. The content of nanobubbles can be arbitrarily selected in consideration of occurrence of a cavitation effect, which will be described later. For example, the content of nanobubbles is 0.1-20 vol %, and is preferably 5-10 vol %, i.e., $6 \times 10^8$ to $1.2 \times 10^9$/ml.

The material for the drug is not specifically limited as long as the drug can disinfect and sterilize the target. Examples of the drug include a sodium hypochlorite solution, a hydrogen peroxide solution, formalin (formalin cresol and formalin guaiacol), phenol products (phenol, phenol camphor, parachlorophenol camphor, cresatin, guaiacol, and cresol), an iodine product (iodine tincture), an EDTA product, and a calcium hydroxide solution.

As the drug, an antibacterial agent or an antibiotic may be selected. Examples of the antibacterial agent or the antibiotic include a tetracycline hydrochloride solution, ampicillin, imipenem, panipenem, vancomycin, chloramphenicol PBSS, PBSC (penicillin against gram-positive bacteria, bacitracin for penicillin-resistant strains, streptomycin for gram-negative bacteria, and sodium caprylate against yeast), ofloxacin, levofloxacin, metronidazole, cefaclor, ciprofloxacin, imidazole, a cathepsin K inhibitor, BMPs, and bFGF.

Nanobubbles include: vesicles made of lipid; and a gas or a gas precursor filling the vesicles.

The diameter of each nanobubble is 10-500 nm, and preferably 100-400 nm in consideration of the complex structure of a root canal, reachability to deep tissue, and stability, for example. The above-mentioned diameter ranges of nanobubbles enable the drug to reach apical areas, lateral branches, and dentin tubules, for example. The diameter of nanobubbles is measured with a nanoparticle size analyzer (SALD-7100, Shimadzu Corporation), for example.

The lipid composition, charged state, density, weight, and particle size, for example, of nanobubbles can be appropriately determined depending on, for example, properties of a target lesion.

Lipid for use in preparing vesicles is not specifically limited, and includes membrane components containing lipids. Examples of the lipids include phospholipid, glycoglycerolipid, sphingoglycolipid, and cationic lipids obtained by introducing a primary amino group, a secondary amino group, a tertiary amino group, or a quaternary ammonium group into these lipids.

Examples of the phospholipids include phosphatidylcholine (e.g., soybean phosphatidylcholine, egg yolk phosphatidylcholine, dilauroylphosphatidylcholine, dimyristoylphosphatidylcholine, dipentadecanoylphosphatidylcholine, dioleoylphosphatidylcholine, dipalmitoylphosphatidylcholine, or distearoylphosphatidylcholine), phosphatidylethanolamine (e.g., dilauroylphosphatidylethanolamine, dimyristoylphosphatidylethanolamine, dioleoylphosphatidylethanolamine, dip almitoylphosphatidylethanolamine, or distearoylphosphatidylethanolamine), phosphatidylserine (e.g., dilauroylphosphatidylserine, dimyristoylphosphatidylserine, dipalmitoylphosphatidylserine, or distearoylphosphatidylserine), phosphatidic acid, phosphatidylglycerol (e.g., dilauroylphosphatidylglycerol, dimyristoylphosphatidylglycerol, dipalmitoylphosphatidylglycerol, or distearoylphosphatidylglycerol), phosphatidylinositol (dilauroylphosphatidylinositol, dimyristoylphosphatidylinositol, dipalmitoylphosphatidylinositol, or distearoylphosphatidylinositol), lysophosphatidylcholine, sphingomyelin, and natural or synthetic phospholipids such as egg yolk lecithin, soybean lecithin, or hydrogenated phospholipids.

Glycoglycerolipid is not specifically limited. Examples of the glycoglycerolipid include sulfoxyribosylglyceride, diglycosyldiglyceride, digalactosyldiglyceride, galactosyldiglyceride, and glycosyldiglyceride.

Sphingoglycolipid is not specifically limited. Examples of the sphingoglycolipid include galactosylcerebroside, lactosylcerebroside, and ganglioside.

Cationic lipid is not specifically limited. Examples of the cationic lipid include lipids in which an amino group, an alkylamino group, a dialkylamino group, or a quaternary ammonium group such as a trialkylammonium group, a monoacyloxyalkyl-dialkylammonium group or a diacyloxyalkyl-monoalkylammonium group, is introduced into the above phospholipids, glyceroglycolipids or sphingoglycolipids. Examples of polyalkylene glycol-modified lipids include lipids in which the above phospholipids, glyceroglycolipids, or sphingoglycolipids are modified with, for example, polyethylene glycol, polypropylene glycol, such as di-$C_{12-24}$acyl-glycerol-phosphatidylethanolamine-N-PEG.

In addition, niosomes such as polyoxyethylene aliphatic acid ester, polyoxyethylene fatty alcohol, polyoxyethylene fatty alcohol ether, polyoxyethylated sorbitan aliphatic acid ester, glycerol polyethylene glycol oxystearate, glycerol polyethylene glycol ricinoleate, ethoxylated soybean sterols, ethoxylated castor oil, polyoxyethylene-polyoxypropylene polymer, and polyoxyethylene aliphatic acid stearate, can be used.

Further, sterol aliphatic acid esters, including cholesterol sulfate, cholesterol butyrate, cholesterol iso-butyrate, cholesterol palmitate, cholesterol stearate, lanosterol acetate, ergosterol palmitate, and phytosterol n-butyrate, can be used.

Sterol esters of sugar acids, including cholesterol glucuronide, lanosterol glucuronide, 7-dehydrocholesterol glucuronide, ergosterol glucuronide, cholesterol gluconate, lanosterol gluconate, and ergosterol gluconate, can also be used.

Esters of sugar acids and alcohols, including lauryl glucuronide, stearoyl glucuronide, myristoyl glucuronide, lauryl gluconate, myristoyl gluconate, and stearoyl gluconate, can also be used.

Esters of sugars and aliphatic acids, including sucrose laurate, fructose laurate, sucrose palmitate, sucrose stearate, glucuronic acid, accharic acid, and polyuronic acid, can also be used.

Saponins, including sarsasapogenin, smilagenin, hederagenin, oleanolic acid, and digitoxigenin, can also be used.

Glycerols and glycerol esters, including glycerol dilaurate, glycerol trilaurate, glycerol dipalmitate, glycerol tripalmitate, glycerol distearate, glycerol tristearate, glycerol dimyristate, and glycerol trimyristate, can also be used.

Long chain alcohols, including n-decyl alcohol, lauryl alcohol, myristyl alcohol, cetyl alcohol and n-octadecyl alcohol, can also be used.

Further, 6-(5-cholesten-3β-yloxy)-1-thio-β-D-galactopyranoside; digalactosyldiglyceride; 6-(5-cholesten-3β-yloxy) hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl) carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoylphosphatidylethanol-amine; 1,2-dioleoyl-sn-glycerol; 1,2-dipalmitoyl-sn-3-succinylglycerol;

1,3-dipalmitoyl-2-succinylglycerol; 1-hexadecyl-2-palmitoylglycerophosphoethanolamine, and palmitoylhomocysteine, can be used.

The nanobubbles may include other materials as a membrane component, as necessary. For example, as a membrance stabilizer, sitosterol, cholesterol, dihydrocholesterol, cholesterol ester, phytosterol, stigmasterol, campesterol, cholestanol, lanosterol, 1-O-sterol glucoside, 1-O-sterol maltoside, or a mixture thereof, can be included.

The weight of the nanobubbles is not specifically limited, and can be increased by filling liposomes with a high-density solution of, for example, cesium chloride. The density of the nanobubbles can be increased by incorporating polysaccharides such as dextran or sulfate in liposomes.

A gas or a gas precursor which can be included in the nanobubbles is as follows:

Perfluorocarbons, such as perfluoromethane, perfluoroethane, perfluoropropane, perfluoroisobutane, perfluoronormalbutane, perfluoro-1-butene, perfluoro-2-butene, perfluoro-2-butyne, perfluorocyclobutene, perfluoroisopentane, perfluoronormalpentane, perfluoroisohexane, perfluoronormalhexane, perfluoroisoheptane, perfluoronormalheptane, perfluoroisooctane, perfluoronormaloctane, perfluorodecalin, perfluorododecalin, perfluorodimethylamine, perfluoroethylene amine, perfluoropent-1-ene, pentafluoro octadecyl iodide, perfluoro-octyl bromide (PFOB), perfluoro-octyliodide, perfluorotripropylamine, and perfluorotributylamine, can be used. The perfluorocarbons can be captured in liposomes, or stabilized in emulsion.

Lauryl trimethyl ammonium bromide (dodecyl-), cetyl trimethyl ammonium bromide (hexadecyl-), myristyl trimethyl ammonium bromide (tetradecyl-), alkyl dimethyl benzilammonium chloride (alkyl=C12, C14, C16), benzyl dimethyl dodecyl ammonium bromide/chloride, benzyl dimethyl hexadecyl ammonium bromide/chloride, benzyl dimethyl tetradecyl ammonium bromide/chloride, cetyl dimethyl ethyl ammonium bromide/chloride, or cetyl pyridinium bromide/chloride, can also be used.

Hexafluoroacetone, isopropylacetylene, allene, tetrafluoroallene, boron trifluoride, isobutane, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, decafluorobutane, 1-butene, 2-butene, 2-methyl-1-butene, 3-methyl-1-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, 2-bromo-butyraldehyde, carbonyl sulfide, crotononitrile, cyclobutane, methylcyclobutane, octafluorocyclobutane, 3-chlorocyclopentene, octafluorocyclopentene, cyclopropane, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis(dimethylphosphine)-amine, 2,3-dimethyl-2-norbornane, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, hexafluoroethane, nitropentafluoroethane, nitrosopentafluoroethane, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neon, neopentane, nitrogen ($N_2$), nitrous oxide, 1,2,3-nonadecane-tricarboxylic acid 2-hydroxytrimethyl ester, 1-nonene-3-yne, oxygen ($O_2$), 1,4-pentadiene, n-pentane, 4-amino-4-methylpentan-2-one, 1-pentene, 2-pentene (cis), 2-pentene (trans), 3-bromopent-1-ene, tetrachlorophthalic acid, 2,3,6-trimethyl-piperidine, propane, 1,1,1,2,2,3-hexafluoropropane, 1,2-epoxypropane, 2,2-difluoro-propane, 2-aminopropane, 2-chloropropane, heptafluoro-1-nitropropane, heptafluoro-1-nitrosopropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur hexafluoride, sulfur (di)-decafluoride ($S_2F_{10}$), 2,4-diaminotoluene, trifluoroacetonitrile, trifluoromethyl peroxide, trifluoromethyl sulfide, tungsten hexafluoride, vinyl acetylene, vinyl ether, and xenon, can also be used.

The particle size of the nanobubbles tends to increase with time after formation, and finally reaches 5 μm or more. Without opening, the particle size of the nanobubbles can be changed within 100-2,000 nm by mixing at 6,500 rpm for 30 seconds with a Lysis and Homogenization Automated Equipment (PRECELLYS24, NEPA GENE, Co., Ltd.).

Figure 5:
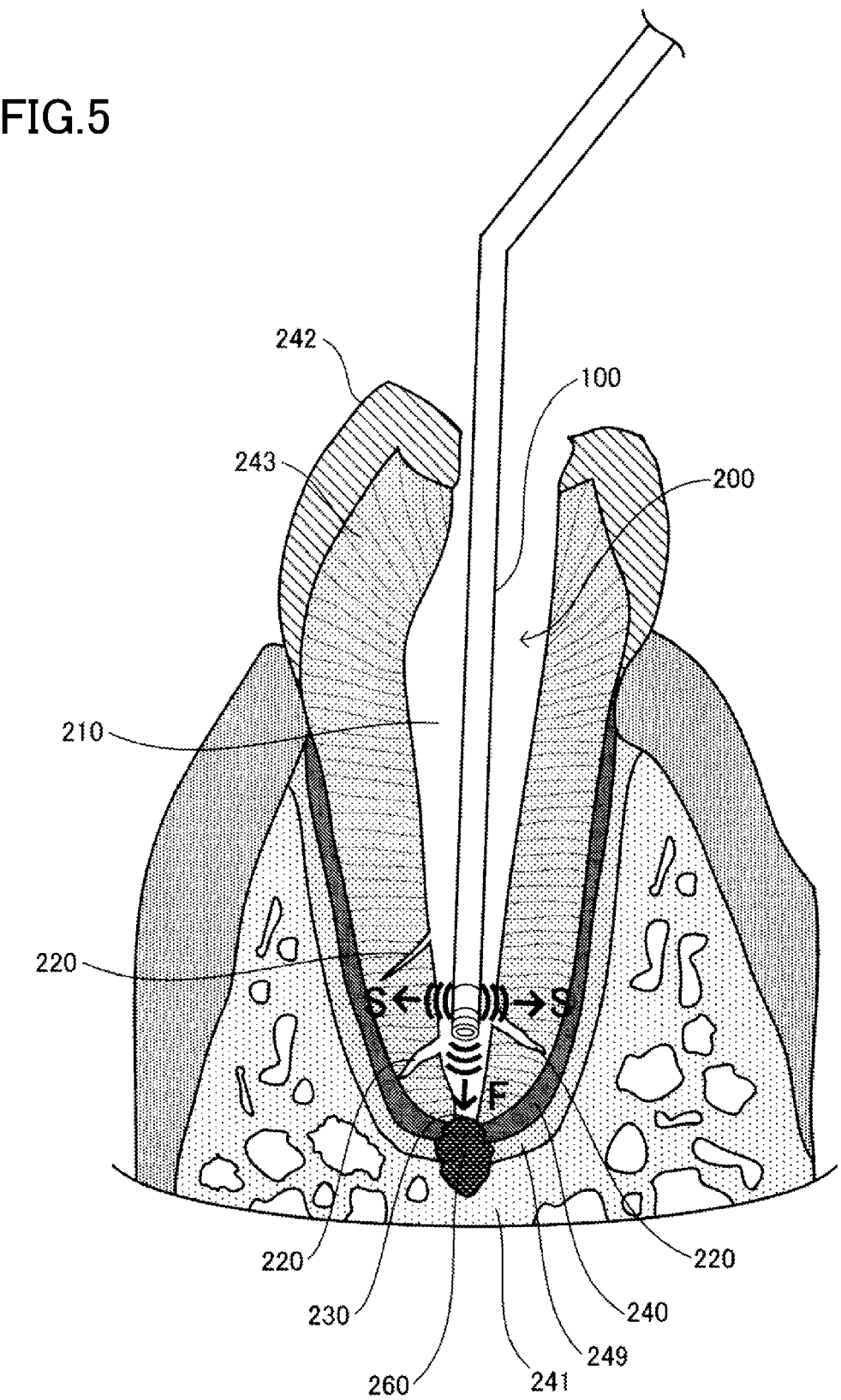
FIG. 5 is a view schematically illustrating a state in which the root canal insertion probe is inserted into a root canal as a target to deliver a drug to the inside of the root canal using ultrasound.

A mode of use of the dental ultrasonic drug delivery system 900 of this embodiment will now be described. FIG. 5 is a view schematically illustrating a state in which the root canal insertion probe 100 of the dental ultrasonic drug delivery system 900 of this embodiment is inserted into a root canal 200 as a target so that the inside of the root canal 200 is sterilized.

The root canal 200 includes a hollow main root canal 210 and lateral branches 220 which are small branches of the main root canal 210. Dentin 243 is covered with enamel 242 at the top, and is fixed by cementum 240, periodontium 249, and alveolar bone 241 at the bottom. A periapical lesion 260 is present under an apical area 230 of the root canal 200. A periapical lesion is also called a periapical lesion or periapical periodontitis, and a general term of lesions of diseases occurring near the apexes of tooth roots (e.g., periapical granuloma and apical periodontal cyst).

A drug mixture, a mixture of nanobubbles and a drug, is injected into the root canal 200 with an injector such as a syringe or a pipette before the root canal insertion probe 100 is inserted into the root canal 200.

Then, the root canal insertion probe 100 is inserted into the root canal 200, and the apical area irradiation part 110 and the lateral branch irradiation part 120 are operated by the manipulation section 160. Since the piezoelectric element 122 of the lateral branch irradiation part 120 vibrates perpendicularly to the axis of the root canal insertion probe 100, ultrasonic energy is also applied sideways as indicated by the arrows S. Thus, ultrasound is applied from the lateral branch irradiation part 120 toward the lateral branches 220 of the root canal 200, thereby causing cavitation in small branch structures of the lateral branches 220. Cavitation is a phenomenon in which gas dissolved in an aqueous solution becomes air bubbles or minute bubbles already present in the solution become air bubbles through repetitive vibration or expansion and shrinkage, under some acoustic vibration conditions. Since nanobubbles are contained in the drug mixture, the energy threshold level for cavitation production decreases. In cavitation, ultrasonic energy is concentrated in a micro region, and cavitation causes small shock waves, thereby increasing cell transmissivity. In addition, cavitation destroys nanobubbles, and the shock of the destruction causes the drug to reach the insides of the complex structure of the root canal and dentin tubules. In this manner, bacteria in the lateral branches 220 can be efficiently killed with the drug. The technique of this embodiment is more advantageous than conventional techniques in which the target is merely embrocated or patched with a drug because the drug more deeply permeates the complex parts of the root canal and dentin tubules to ensure prompt sterilization.

Figure 6A:
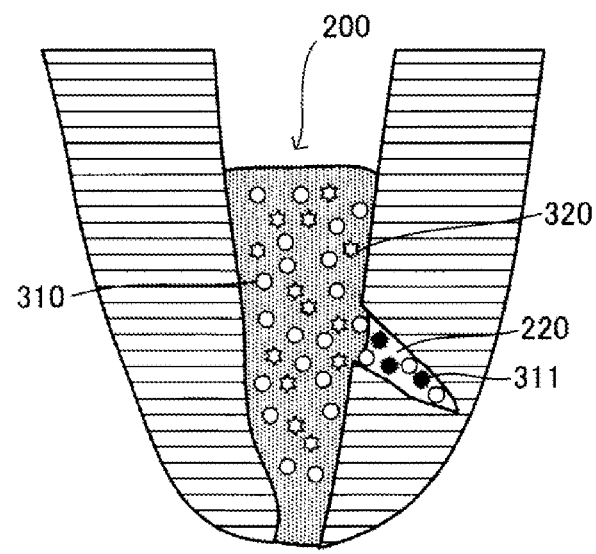
FIG. 6A is an illustration of a state in which a drug mixture is injected into a root canal.
Figure 6B:
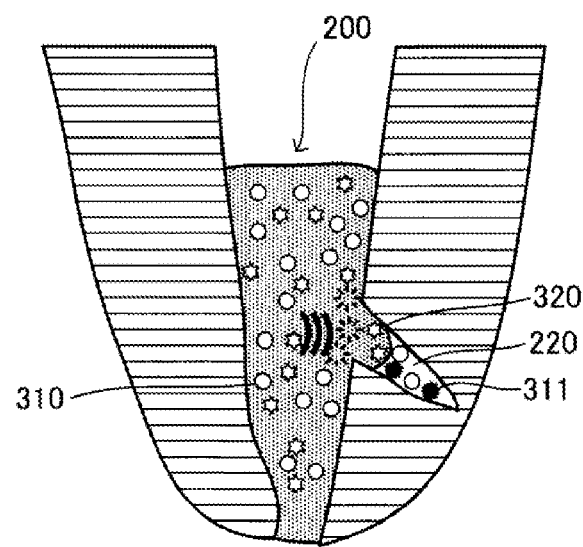
FIG. 6B is an illustration of a state in which ultrasound is applied toward a lateral branch.
Figure 6C:
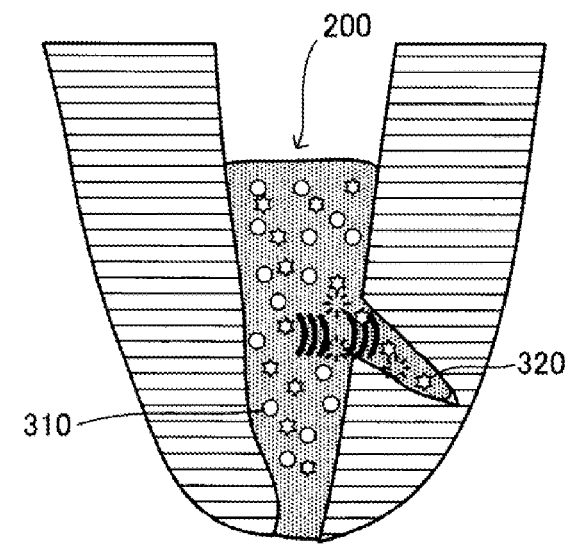
FIG. 6C is an illustration of a state in which nanobubbles in the root canal and the lateral branch are destroyed and a drug is delivered toward the lateral branch so that bacteria are killed.

FIGS. 6A, 6B, and 6C are illustrations of sterilization of a lateral branch. With reference to FIGS. 6A, 6B, and 6C, sterilization of the lateral branches 220 will be further described. FIG. 6A is an illustration of a state in which a drug mixture is injected into a root canal. FIG. 6B is an illustration of a state in which ultrasound is applied toward a lateral branch. FIG. 6C is an illustration of a state in which nanobubbles in the root canal and the lateral branch are destroyed and a drug is delivered toward the lateral branch so that bacteria are killed. As illustrated in FIG. 6A, in a state in which a drug mixture has been injected into the root canal 200, nanobubbles 310 permeate the lateral branch 220, but a drug 320 does not easily permeate the lateral branch 220. Accordingly, bacteria 311 which have invaded the lateral branch 220 are not killed. Next, as illustrated in FIG. 6B, when ultrasound is applied from a root canal insertion probe (not shown) toward the lateral branch, nanobubbles 310 near the lateral branch are destroyed, and cavitation occurs accordingly. This cavitation effect allows the drug 320 to permeate the lateral branch 220. Further, as illustrated in FIG. 6C, as the ultrasound travels in the lateral branch 220, nanobubbles 310 in the lateral branch 220 are destroyed, and cavitation occurs accordingly, resulting in that the drug 320 further permeates deeper areas of the lateral branch 220. In this manner, bacteria 311 in the lateral branch 220 are killed as intended.

In this embodiment, since bubbles mixed with the drug 320 are nanobubbles 310, the cavitation effect can occur with a relatively low energy.

Figure 7A:
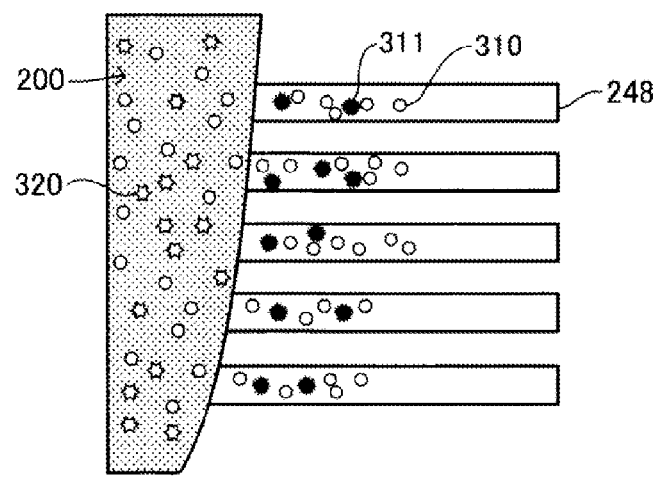
FIG. 7A is a conceptual illustration of sterilization of bacteria in dentin tubules of a root canal, and shows a state in which a drug mixture is injected into the root canal.
Figure 7B:
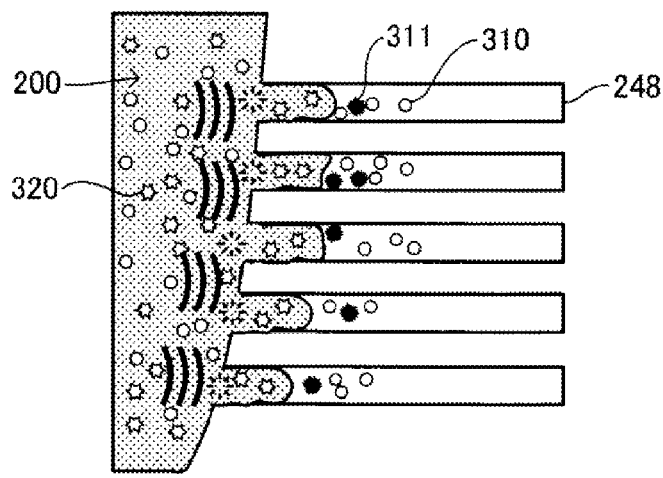
FIG. 7B is a conceptual illustration of sterilization of bacteria in dentin tubules of a root canal, and shows a state in which ultrasound is applied toward the dentin tubules so that nanobubbles are destroyed.
Figure 7C:
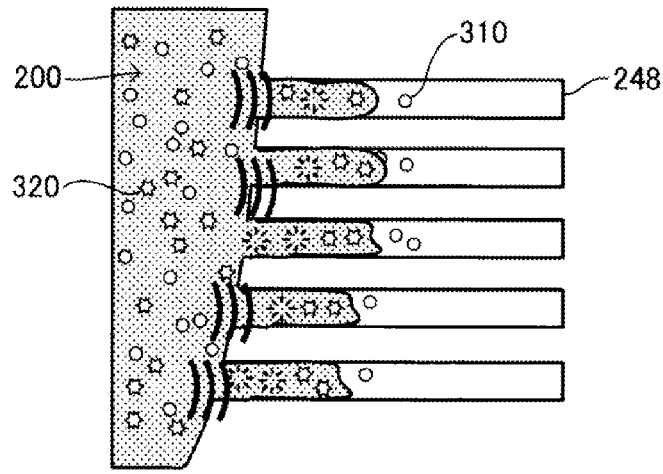
FIG. 7C is a conceptual illustration of sterilization of bacteria in dentin tubules of a root canal, and shows a state in which a drug permeates the dentin tubules so that bacteria are killed.

FIG. 7A is an illustration of a state in which a drug mixture is injected into the root canal 200. FIG. 7B is an illustration of a state in which ultrasound is applied toward the dentin tubules 248 so that nanobubbles are destroyed. FIG. 7C is a conceptual illustration of sterilization of bacteria 311 in dentin tubules 248 of the root canal 200, and shows a state in which a drug permeates the dentin tubules 248 so that bacteria are killed.

As illustrated in FIG. 7A, the dentin tubules 248 are tubular, and dentin is constituted by a collection of the dentin tubules 248. In a state in which a drug mixture has been injected into the root canal 200, nanobubbles 310 permeate the dentin tubules 248, but the drug 320 does not easily permeate the dentin tubules 248. Accordingly, bacteria 311 which have invaded the dentin tubules 248 are not killed.

Next, as illustrated in FIG. 7B, when ultrasound is applied from a root canal insertion probe (not shown) toward the dentin tubules 248, nanobubbles 310 near the dentin tubules 248 are destroyed, and cavitation occurs accordingly. This cavitation effect allows the drug 320 to permeate the dentin tubules 248.

Further, as illustrated in FIG. 7C, as the ultrasound travels in the dentin tubules 248, nanobubbles 310 in the dentin tubules 248 are destroyed, and cavitation occurs accordingly, resulting in that the drug 320 further permeates deeper areas of the dentin tubules 248. In this manner, the drug reaches bacteria 311 in deeper areas of the dentin tubules 248 as intended, thus promptly achieving perfect sterilization.

Referring back to FIG. 5, since the piezoelectric element 112 of the apical area irradiation part 110 vibrates in the axial direction of the root canal insertion probe 100, ultrasonic energy is also applied forward as indicated by the arrow F. In this manner, ultrasonic energy is applied toward the apical area 230 of the root canal 200, and cavitation occurs in the periapical lesion 260. In the same manner as sterilization in the lateral branches 220 described above, bacteria in the periapical lesion 260 can be efficiently killed with the drug as intended.

Since the root canal 200 has small branches of accessory canals and lateral branches 220, the current root canal treatment is effective only for the main root canal 210 even by means of pulpectomy and an infected root canal treatment, and it is still difficult to sufficiently enlarge and clean the accessory canals and the lateral branches 220. Thus, the current infected root canal treatment is considered as a treatment which leaves a considerable amount of pathogenesis factors, and it is difficult to predict prognoses accurately. In addition, aging alteration further closes and complicates the root canal 200 through calcification. In this case, it is more difficult to predict prognoses after an infected root canal treatment. According to the present disclosure, however, ultrasound is applied from the lateral branch irradiation part 120 toward the lateral branches 220 to clean and sterilize small areas of accessory canals and the lateral branches 220. Thus, not only without aging alteration but also with aging alteration, accurate prediction of prognoses can be ensured.

In the case of a root canal 200 which is significantly curved in its apical area 230, it is difficult to conduct a root canal treatment. However, even in this case, the technique of this embodiment is advantageous because ultrasound is applied from the apical area irradiation part 110 and the lateral branch irradiation part 120 so that small areas of even the significantly curved root canal 200 can be cleaned and sterilized.

(Second Embodiment)

A second embodiment is different from the first embodiment in that an ultrasonic transducer is provided not on the proximal end of the root canal insertion probe 100 but in the probe body 150.

Figure 8A:
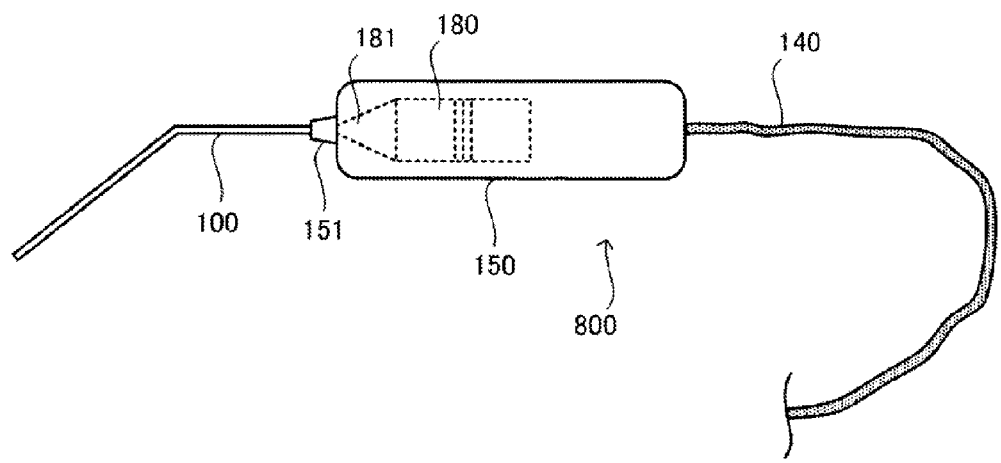
FIG. 8A is a view illustrating an ultrasonic delivery device in which a Langevin transducer is provided inside a probe body.
Figure 8B:
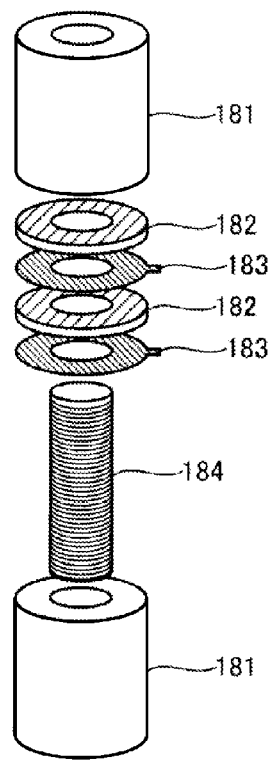
FIG. 8B is a view illustrating the Langevin transducer.

FIG. 8A is a view illustrating an ultrasonic delivery device 800 in which a Langevin transducer 180 is provided inside a probe body 150. FIG. 8B is a view illustrating the Langevin transducer 180.

As illustrated in FIG. 8A, the Langevin transducer 180 is provided in the probe body 150. A manipulation section 160 has the same configuration as that of the first embodiment. The probe body 150 is provided with a fixing screw 151. A root canal insertion probe 100 is detachably fixed to the probe body 150 with the fixing screw 151 interposed therebetween. A vibration amplitude amplification horn 181 is coupled and fixed to the front end of the Langevin transducer 180 to be integrated with the Langevin transducer 180. A root canal insertion probe 100 is coupled to the vibration amplitude amplification horn 181. The root canal insertion probe 100 may be removed, and replaced with a dental caries therapeutic probe 130, which will be described later. The root canal insertion probe 100 may be integrated with the probe body 150.

As illustrated in FIG. 8B, the Langevin transducer 180 is a rod-integrated Langevin transducer including: a bolt rod 184; piezoelectric elements 182 each made of a ring-shaped flat plate having an opening larger than the bolt rod 184; electrode plates 183 which have substantially the same outer and inner diameters as those of the piezoelectric elements 182 and are thinner than the piezoelectric elements 182; and metal blocks 181 through which ultrasound propagates to the dental caries therapeutic probe 130. The piezoelectric elements 182 and the electrode plates 183 are alternately stacked such that the bolt rod 184 is inserted into the center openings thereof and located on the same axis as those of the piezoelectric elements 182 and the electrode plates 183. The configuration of the rod-integrated Langevin transducer can provide resonance at a relatively low frequency, and when tightened with bolts, can endure a large vibration amplitude and operate as a tough high-power transducer.

Ultrasound generated by the Langevin transducer 180 propagates through the root canal insertion probe 100, and is emitted from the distal end of the Langevin transducer 180. In this manner, as in the first embodiment, small areas of the complex structure of the root canal 200 can be cleaned and sterilized.

(Third Embodiment)

In the first and second embodiments, the probe attached to the probe body 150 is a root canal insertion probe configured to be inserted into a root canal. Unlike these embodiments, a third embodiment employs a dental caries therapeutic probe which is used while being positioned against a dental caries portion.

Figure 9:
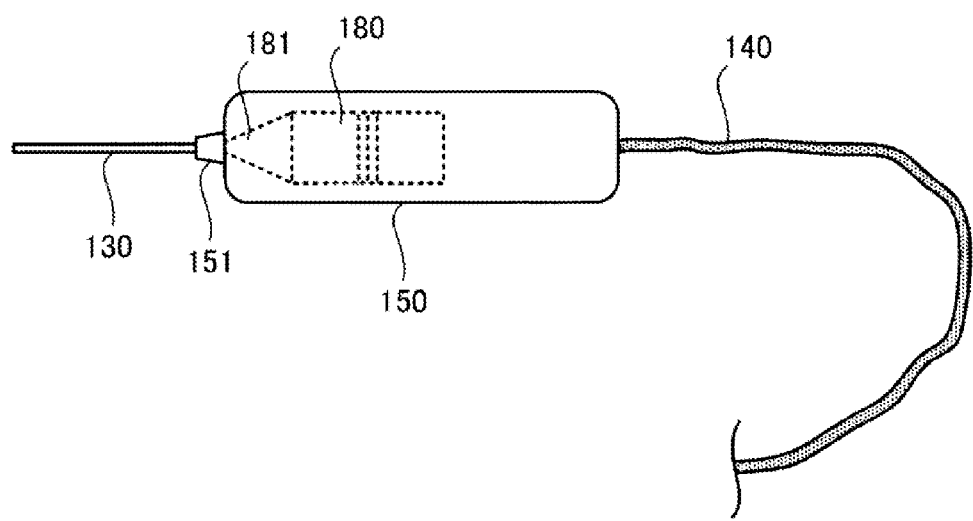
FIG. 9 is a view illustrating a probe body to which a dental caries therapeutic probe is attached.

FIG. 9 is a view illustrating a probe body 150 to which a dental caries therapeutic probe 130 is attached. As in the second embodiment, a Langevin transducer 180 is provided in the probe body 150, and as illustrated in FIG. 8B, ultrasound propagates through a metal block 181. The configuration of a manipulation section 160 is the same as that of the first embodiment.

Unlike a root canal insertion probe 100, the dental caries therapeutic probe 130 is linear. The size of the dental caries therapeutic probe 130 is not specifically limited as long as the dental caries therapeutic probe 130 can be used while being positioned against a dental caries portion. For example, the diameter of the dental caries therapeutic probe 130 is 2 mm to 8 mm, and preferably 3 mm to 6 mm. The length of the dental caries therapeutic probe 130 is not specifically limited, and is, for example, 1 cm to 5 cm, preferably 2 cm to 4 cm, and more preferably 3 cm. As a material for the dental caries therapeutic probe 130, a lightweight material which is resistant to corrosion is preferably used, and stainless used steel (SUS) may be used.

The frequency of ultrasound is not specifically limited as long as cavitation occurs to allow a drug to permeate a dental caries portion and dentin tubules, as will be described later. The frequency of ultrasound is, for example, 100 KHz to 10 MHz, preferably 800 KHz to 2 MHz, and particularly preferably about 1 MHz.

The intensity of ultrasound is not specifically limited as long as cavitation occurs in a preferable manner without damaging dental tissue of, for example, dentin and dental pulp. The intensity of ultrasound is, for example, 1-30 W/cm$^2$, preferably 10-25 W/cm$^2$, and particularly preferably about 20 W/cm$^2$.

As in the first embodiment, a drug for sterilizing a dental caries portion can be delivered in a mixed state with nanobubbles. The drug and the nanobubbles used in the first embodiment can be employed in the third embodiment.

Figure 10:
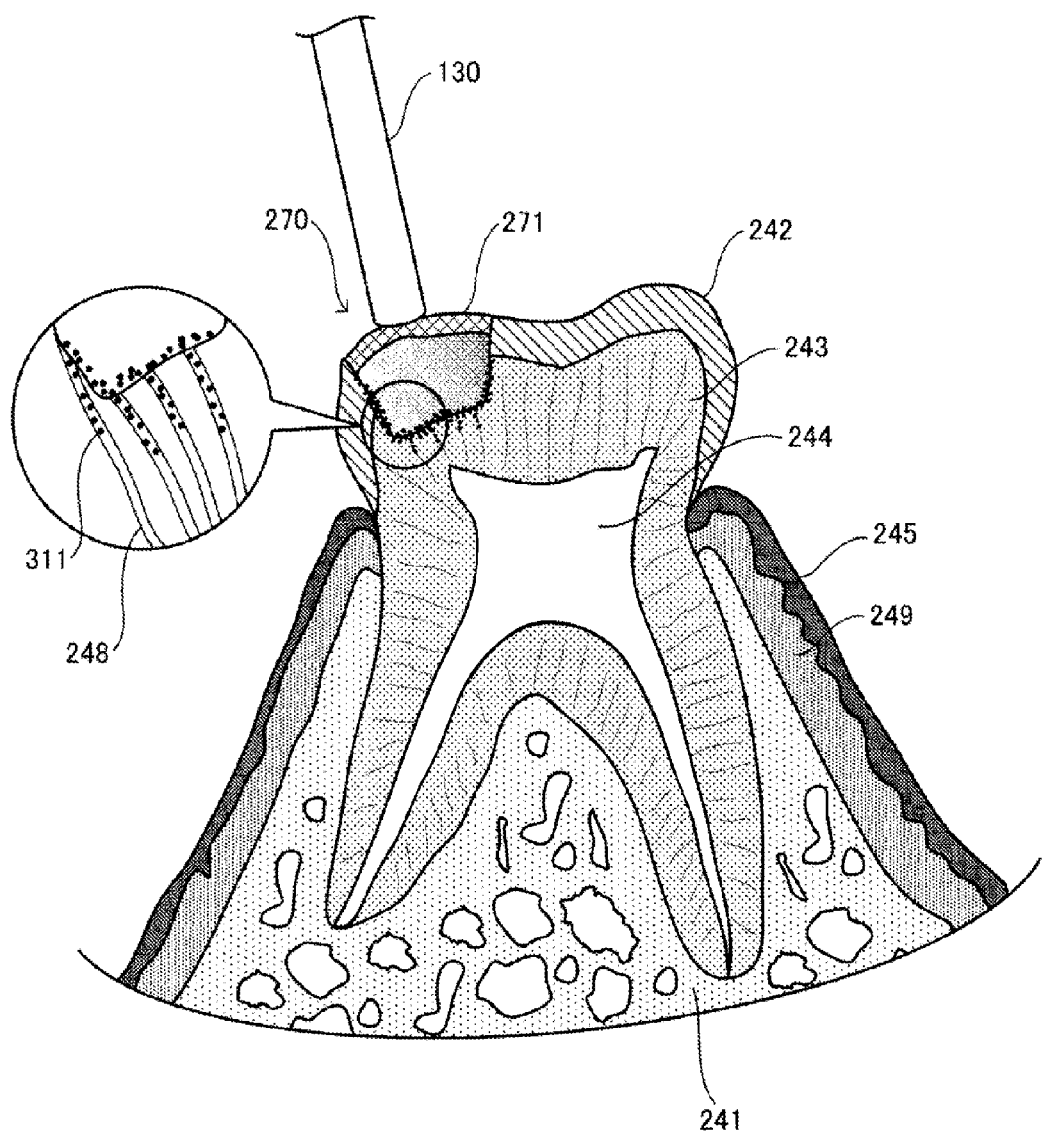
FIG. 10 is a view schematically illustrating a state in which the dental caries therapeutic probe is pressed against a dental caries portion, which is a target of treatment, to deliver a drug to the dental caries portion.

A mode of use of a dental ultrasonic drug delivery system 900 of this embodiment will now be described. FIG. 10 is a view schematically illustrating a state in which the dental caries therapeutic probe 130 of the dental ultrasonic drug delivery system 900 of this embodiment is pressed against a dental caries portion 270, which is a target of treatment, to sterilize the dental caries portion 270.

Dental pulp 244 is covered with dentin 243, which is covered with enamel 242. A tooth root is protected by a periodontium 249 and a dental cervix mucosal epithelium 245 formed on the periodontium 249, and is fixed by alveolar bone 241. A tooth crown has a dental caries portion 270. A dental caries portion is a substantial missing portion of a tooth caused when dentin is decalcified by acid produced from carbohydrate by bacteria in the mouth.

A drug mixture, which is a mixture of nanobubbles and a drug, is injected or supplied into the dental caries portion 270 with an injector such as a syringe and a pipette, and the dental caries portion 270 is closed with a gel 271 for ultrasound permeation. The ultrasound permeation gel 271 prevents the drug mixture injected or supplied into the dental caries portion 270 from flowing out from the dental caries portion 270, and also prevents formation of an air layer which serves as a gap when the dental caries therapeutic probe 130 is positioned against the dental caries portion 270. In the state shown in FIG. 10, the dental caries therapeutic probe 130 is positioned against the ultrasound permeation gel 271 to cause ultrasound to propagate. Alternatively, the dental caries therapeutic probe 130 may cause ultrasound to propagate by penetrating into the ultrasound permeation gel 271 so that the distal end thereof reaches near the bottom of the dental caries portion 270.

Then, in the same manner as in the first embodiment, ultrasound is caused to propagate from the distal end of the dental caries therapeutic probe 130 by manipulating the manipulation section 160. Then, cavitation occurs, and destroys nanobubbles. The shock of the destruction allows the drug to reach small areas of the dental caries portion. Accordingly, bacteria in the dental caries portion 270 are efficiently sterilized by the drug.

Figure 11A:
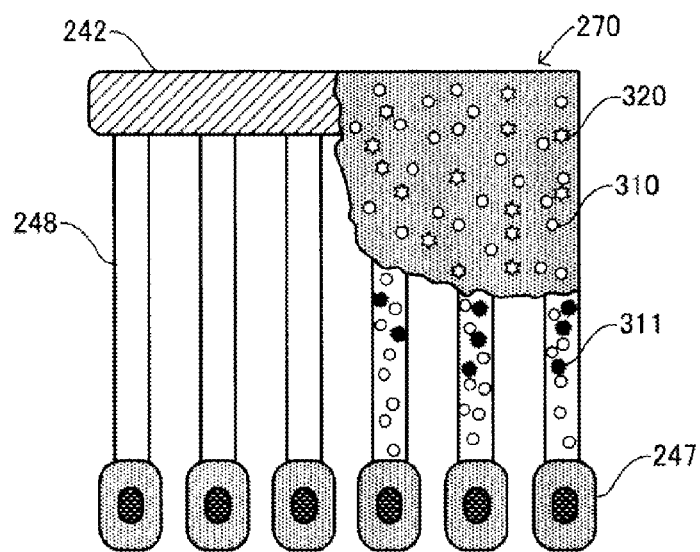
FIG. 11A is an illustration of a state in which a drug mixture is injected into a dental caries portion.
Figure 11B:
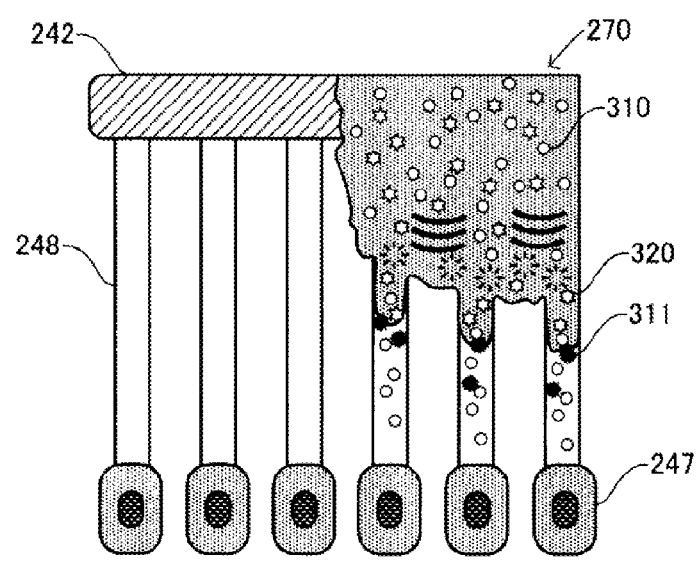
FIG. 11B is an illustration of a state in which ultrasound is applied toward dentin tubules.
Figure 11C:
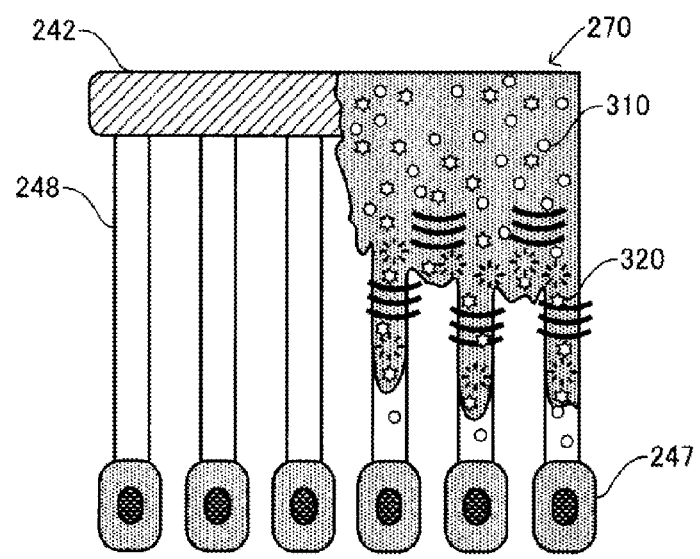
FIG. 11C is an illustration of a state in which nanobubbles in the dentin tubules are destroyed and bacteria are killed.

FIGS. 11A-11C are illustrations of sterilization of bacteria 311 in dentin tubules 248. Irrigation in the dentin tubules 248 will be described with reference to FIGS. 11A-11C. FIG. 11A illustrates a state in which a drug mixture is injected into a dental caries portion 270. FIG. 11B illustrates a state in which ultrasound is applied toward the dentin tubules 248 and nanobubbles are destroyed. FIG. 11C illustrates a state in which the drug permeates the dentin tubules 248 and bacteria are killed.

As illustrated in FIG. 11A, the dentin tubules 248 are tubular, and dentin is constituted by a collection of the dentin tubules 248. In the dentin tubules 248, processes enter from odontoblast 247. Accordingly, when enamel 242 is destroyed and dentin is exposed, which is equivalent to exposure of dental pulp, a pain, such as being hypersensitive to cold things, occurs. In a state in which a drug mixture is injected into the dental caries portion 270, nanobubbles 310 permeate the dentin tubules 248, but the drug 320 does not easily reach the dentin tubules 248. Accordingly, although bacteria 311 are killed by the drug 320 in most part of the dental caries portion 270, bacteria 311 invading as far as the dentin tubules 248 are not killed.

Then, as illustrated in FIG. 11B, when ultrasound is applied from a dental caries therapeutic probe 130 (not shown) toward the dentin tubules 248, nanobubbles 310 near the dentin tubules 248 are destroyed, and cavitation occurs accordingly. This cavitation effect allows the drug 320 to permeate the dentin tubules 248.

Further, as illustrated in FIG. 11C, as the ultrasound travels in the dentin tubules 248, nanobubbles 310 in the dentin tubules 248 are destroyed, and cavitation occurs accordingly, resulting in that the drug 320 further permeates deeper areas of the dentin tubules 248. In a conventional treatment for dental caries, it is difficult to sterilize deep areas of the dentin tubules. The present disclosure, however, ensures that the drug 320 reaches bacteria 311 residing in deep areas of the dentin tubules 248 and promptly achieves perfect sterilization. As a result, dentin/dental pulp regeneration by a cell transplantation therapy or an MMP3 protein therapy is accelerated and reliable therapy can be achieved. If microbubbles (with a diameter of 1 μm to 50 μm) were employed instead of nanobubbles, the microbubbles cannot enter the dentin tubules 248 because the diameter of the dentin tubules 248 is about 500 nm. Thus, unlike the technique of the present disclosure, it is extremely difficult to sterilize the inside of the dentin tubules 248 by means of the cavitation effect.

In the third embodiment, the Langevin transducer 180 is provided in the probe body 150. However, the present disclosure is not limited to this example, and as described in the first embodiment, an ultrasonic transducer including an inner electrode, a piezoelectric element, and an outer electrode may be provided at the distal end of the dental caries therapeutic probe 130.

(Fourth Embodiment)

Unlike the foregoing embodiments, a fourth embodiment employs a probe for periodontal disease therapy mainly used while being inserted into a periodontal pocket.

Figure 12:
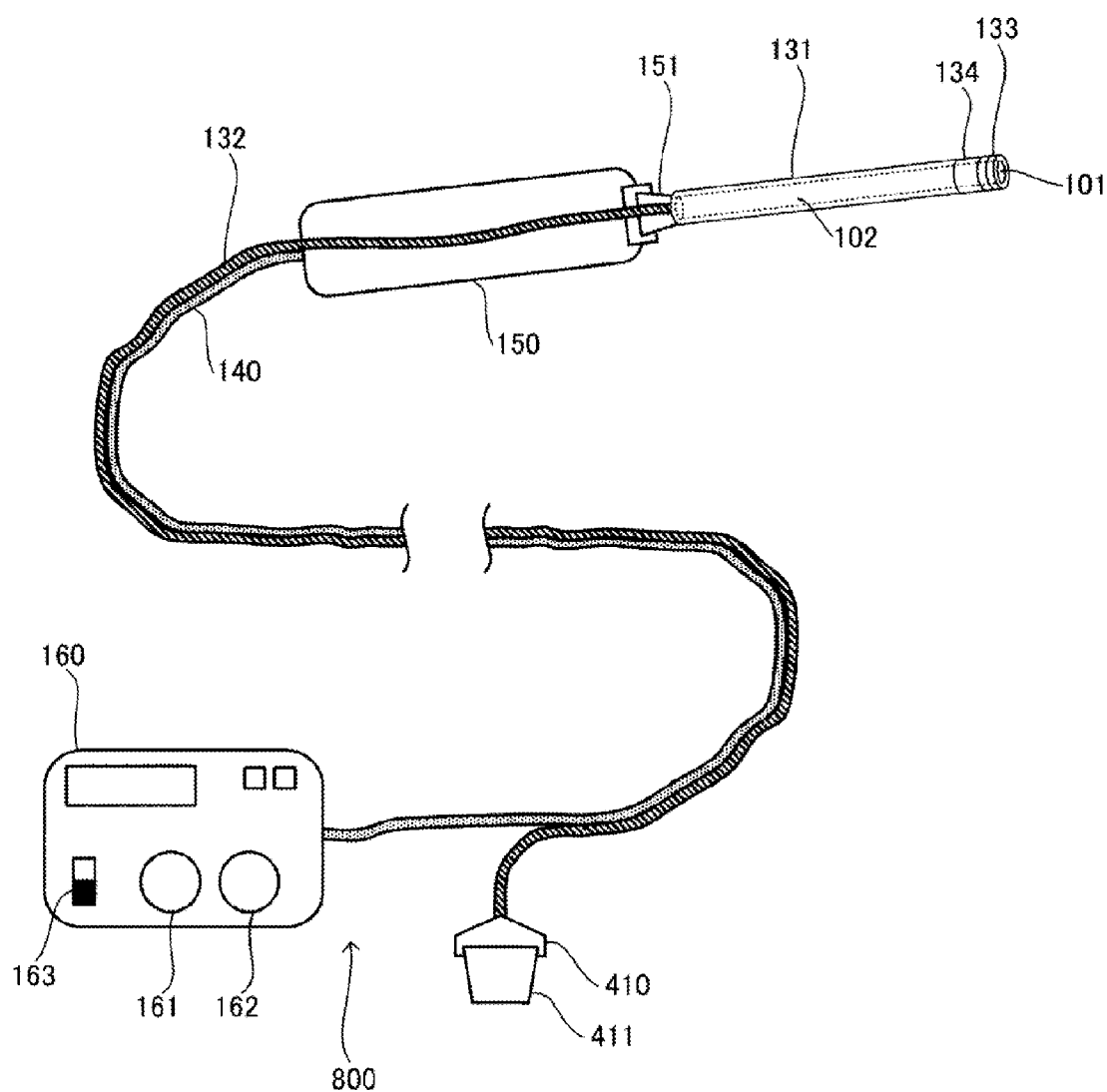
FIG. 12 is a view schematically illustrating an ultrasonic delivery device to which a periodontal disease therapeutic probe is attached.

As illustrated in FIG. 12, an ultrasonic delivery device 800 according to the fourth embodiment includes a periodontal disease therapeutic probe 131 provided in a probe body 150. The periodontal disease therapeutic probe 131 has a tubular shape having an aperture 101 at the distal end thereof and a hollow part 102 therein. As a drug supply system, the ultrasonic delivery device 800 includes: a drug storage part 411 for storing a drug mixture which is a mixture of nanobubbles and a drug; a trigger 410 for ejecting the drug mixture; and a drug tube 132 connecting the trigger 410 to an end of the hollow part 102 such that the drug mixture is delivered from the trigger 410 to the hollow part 102. The other part of the configuration is the same as that in the first embodiment described above. Although the diameter of the periodontal disease therapeutic probe 131 is enlarged for convenience of understanding the drawings, the periodontal disease therapeutic probe 131 is small enough to be inserted into a periodontal pocket.

Figure 13A:
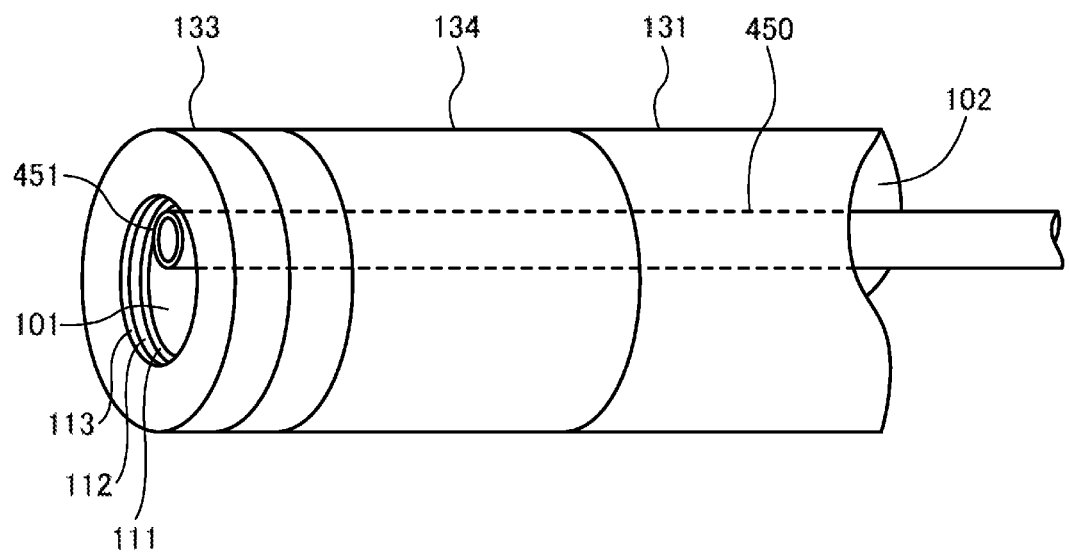
FIG. 13A is a view schematically illustrating a distal end of a periodontal disease therapeutic probe.
Figure 13B:
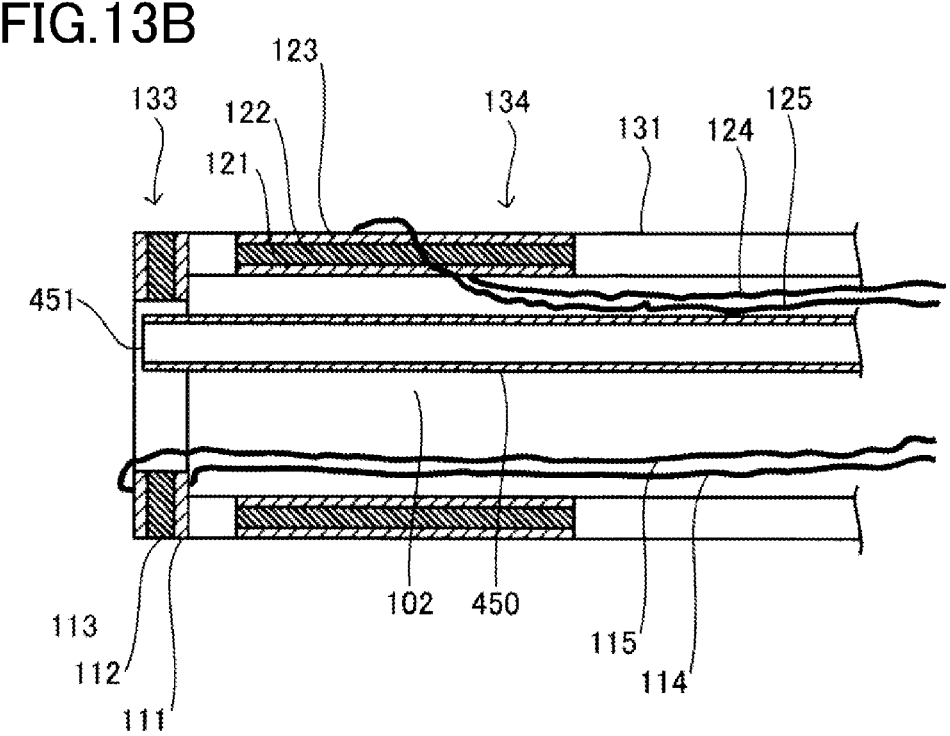
FIG. 13B is a cross-sectional view illustrating the distal end of the periodontal disease therapeutic probe.

FIGS. 13A and 13B are illustrations of the distal end of the periodontal disease therapeutic probe 131. FIG. 13A is an outline view, and FIG. 13B is a cross-sectional view. As illustrated in FIG. 13A, the periodontal disease therapeutic probe 131 includes: a bottom irradiation part 133 for irradiating the bottom of a periodontal pocket with ultrasound; and a side irradiation part 134 for irradiating the side of the periodontal pocket with ultrasound. The bottom irradiation part 133 and the side irradiation part 134 cause ultrasound to propagate a periodontal pocket. The bottom irradiation part 133 is located at the distal end of the periodontal disease therapeutic probe 131, and applies ultrasound in the longitudinal direction of the probe. The side irradiation part 134 is located slightly at the rearward of the distal end of the periodontal disease therapeutic probe 131, and applies ultrasound in the transverse direction of the probe.

As illustrated in FIGS. 13A and 13B, a drug delivery tube 450 is provided in the hollow part 102 inside the periodontal disease therapeutic probe 131. The drug mixture ejected from the trigger 410 passes through the drug delivery tube 450 by way of the drug tube 132, and injected into a periodontal pocket through an aperture 451 of the drug delivery tube 450. The configurations of the bottom irradiation part 133 and the side irradiation part 134 are the same as those in the first embodiment. The bottom irradiation part 133 includes an ultrasonic transducer constituted by: a cylindrical piezoelectric element 112; a tubular inner electrode 111 located on the inner side of the piezoelectric element 112; and a cylindrical outer electrode 113 located on the outer side of the piezoelectric element 112. The side irradiation part 134 includes an ultrasonic transducer constituted by: a cylindrical piezoelectric element 122; a tubular inner electrode 121 located on the inner side of the piezoelectric element 122; and a cylindrical outer electrode 123 located on the outer side of the piezoelectric element 122.

The periodontal disease therapeutic probe 131 is linear. The size of the periodontal disease therapeutic probe 131 is not specifically limited as long as the periodontal disease therapeutic probe 131 can be inserted into a periodontal pocket. For example, the diameter of the periodontal disease therapeutic probe 131 is 0.5 mm to 4 mm, and preferably 0.5 mm to 2 mm. The length of the periodontal disease therapeutic probe 131 is not specifically limited, and is, for example, 1 cm to 5 cm, preferably 2 cm to 4 cm, and more preferably 3 cm. As a material for the dental caries therapeutic probe 130, a lightweight material which is resistant to corrosion is preferably used, and stainless used steel (SUS) may be used.

The frequency of ultrasound is not specifically limited as long as cavitation occurs to allow a drug to permeate a periodontal pocket. The frequency of ultrasound is, for example, 100 KHz to 10 MHz, preferably 800 KHz to 2 MHz, and particularly preferably about 1 MHz.

The intensity of ultrasound is not specifically limited as long as cavitation occurs in a preferable manner without damaging dental tissue. The intensity of ultrasound is, for example, 1-30 W/cm$^2$, preferably 10-25 W/cm$^2$, and particularly preferably about 20 W/cm$^2$.

A drug for use in periodontal disease therapy is delivered in a mixed state with nanobubbles. The drug is not specifically limited. Examples of the drug include isopropyl methyl phenol, thymol, clove oil, dipotassium glycyrrhizinate, allantoin, hinokitiol, cetylpyridinium chloride, panthenol, tocopherol acetate, sodium lauroyl sarcosine, tranexamic acid, ε-aminocaproic acid, bisphosphonate, tetracycline, presteron, minocycline, doxycycline, levofloxacin, ofloxacin, metronidazole, amoxicillin, a cathepsin K inhibitor, chlorhexidine, hypochlorous acid, BMPs, bFGF, and a mixture of one or more of these substances.

Figure 14:
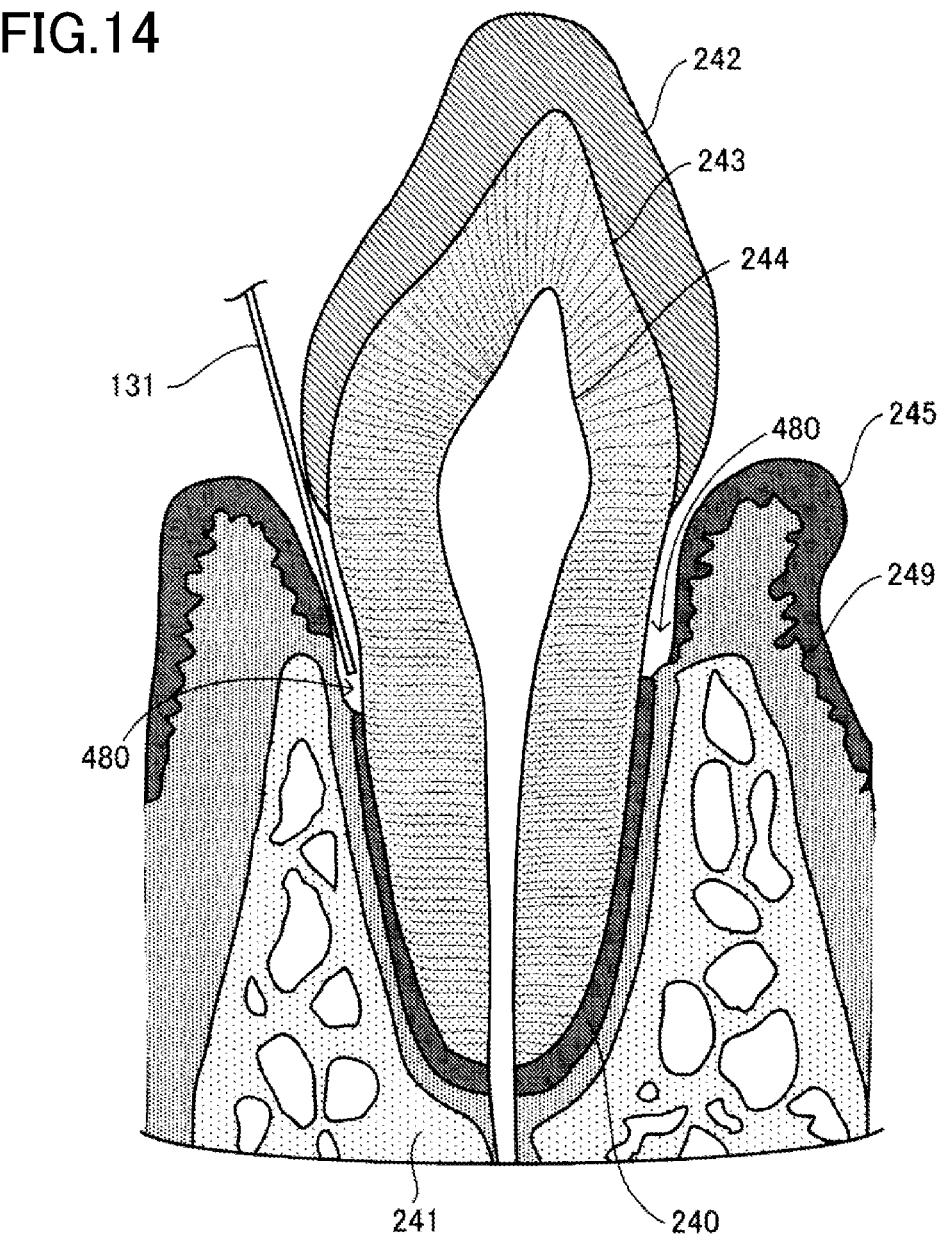
FIG. 14 is a view schematically illustrating a state in which a periodontal disease therapeutic probe is inserted into a periodontal pocket to sterilize the inside of the periodontal pocket.

A mode of use of a dental ultrasonic drug delivery system 900 of this embodiment will now be described. FIG. 14 is a view schematically illustrating a state in which the periodontal disease therapeutic probe 131 of the dental ultrasonic drug delivery system 900 of this embodiment is inserted into a periodontal pocket 480, which is a target of treatment, to sterilize the inside of the periodontal pocket 480.

A tooth is surrounded by gingival sulcus having a depth of 1-2 mm in healthy gums, and 3-5 mm in moderate periodontitis, and 6 mm or more in some cases where periodontal diseases progress. In dental plaque accumulated in the periodontal pocket 480, bacteria easily proliferate, and the progress of inflammation of gingival causes alveolar bone, which should support the tooth, to melt.

A drug mixture is injected from the aperture 451 of the drug delivery tube 450 by manipulating the trigger 410, and in the same manner as in the first embodiment, ultrasound is caused to propagate from the distal end of the periodontal disease therapeutic probe 131 by manipulating the manipulation section 160. Then, cavitation occurs, and destroys nanobubbles. The shock of the destruction allows the drug to reach small areas of the periodontal pocket 480. Accordingly, bacteria in the periodontal pocket 480, cementum, and dentin are efficiently killed by the drug.

As in the first embodiment, the periodontal disease therapeutic probe 131 is detachably fixed to the probe body 150 with the fixing screw 151 interposed therebetween. Specifically, in a case where the root canal insertion probe 100 of the first embodiment is replaced with the periodontal disease therapeutic probe 131 of this embodiment, the root canal insertion probe 100 is detached and replaced with the periodontal disease therapeutic probe 131, and the drug tube 132 to which the trigger 410 is attached is connected to the drug delivery tube 450 provided in the hollow part 102 in the periodontal disease therapeutic probe 131. The periodontal disease therapeutic probe 131 may be integrated with the probe body 150.

Figure 15:
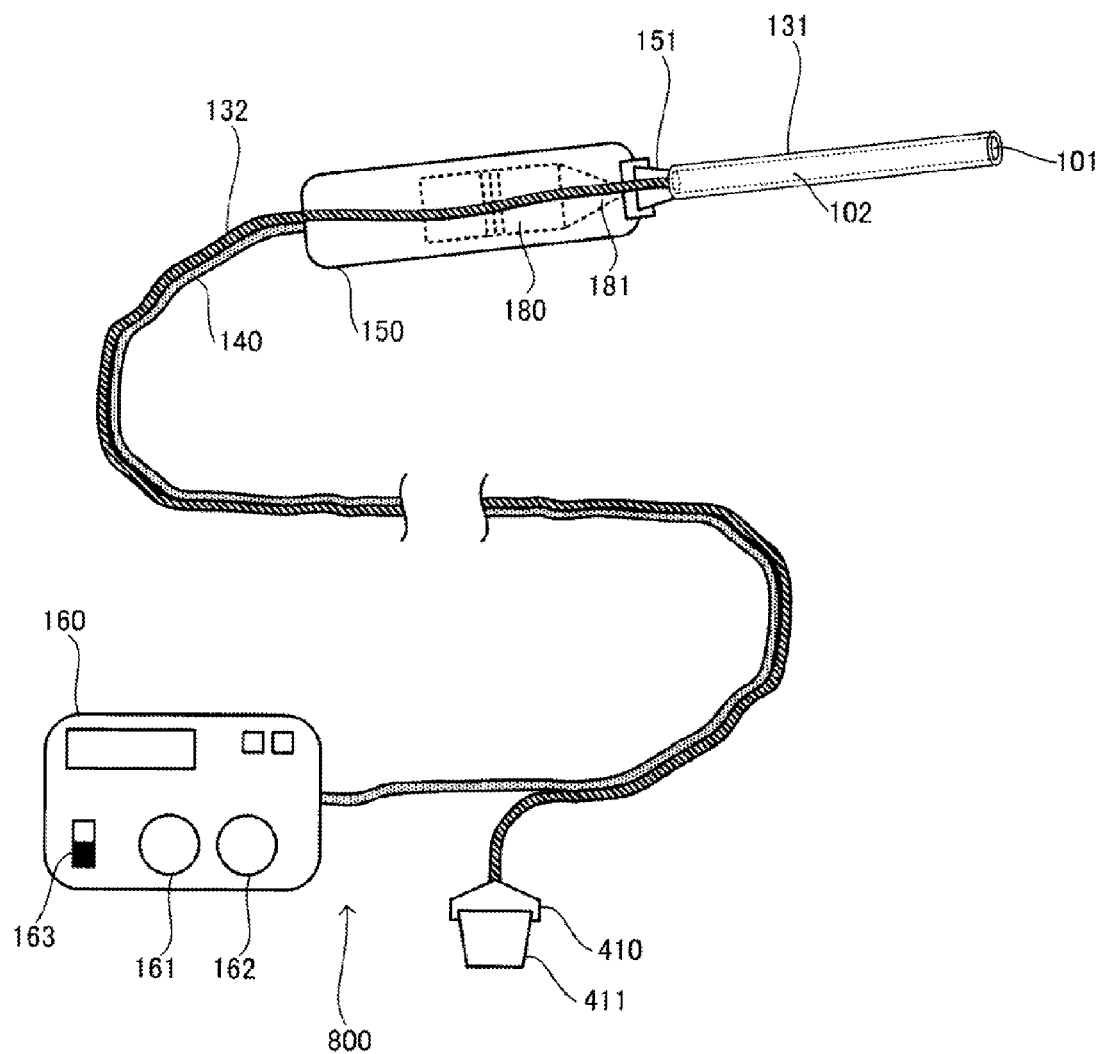
FIG. 15 is a view schematically illustrating a periodontal disease therapeutic probe in a case where a Langevin transducer is provided in a probe body.

FIG. 15 is a view schematically illustrating the periodontal disease therapeutic probe 131 in a case where a Langevin transducer 180 is provided in the probe body 150. The transducer is not necessarily provided at the distal end of the periodontal disease therapeutic probe 131 as in the above embodiments. As illustrated in FIG. 15, the Langevin transducer 180 may be provided in the probe body 150 such that ultrasound is caused to propagate.

In the above embodiments, the drug mixture is injected through the drug delivery tube 450 provided in the hollow part 102. Alternatively, the drug delivery tube 450 does not need to be provided, and the drug mixture may pass directly through the hollow part 102.

(Fifth Embodiment)

Unlike the above embodiments, a fifth embodiment employs a probe for hyperesthesia therapy.

Figure 16:
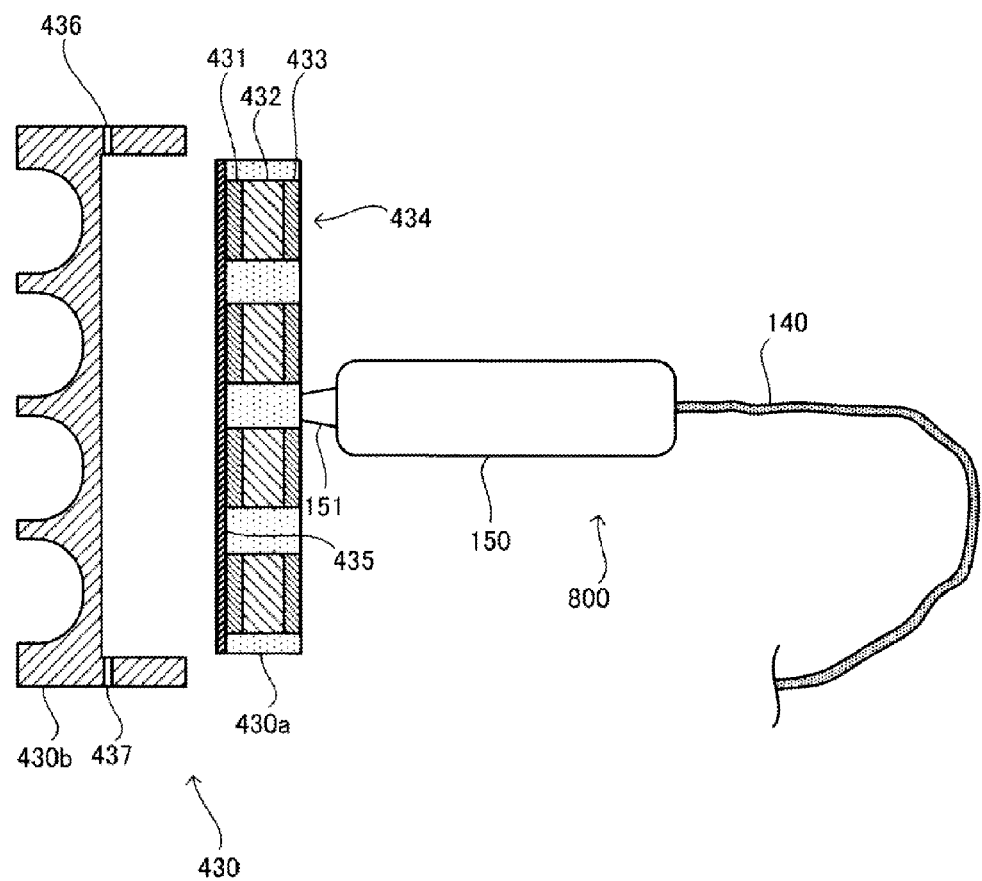
FIG. 16 is an illustration of a probe body to which a hyperesthesia therapeutic probe is attached.

FIG. 16 is an illustration of a probe body 150 to which a hyperesthesia therapeutic probe 430 is attached. As illustrated in FIG. 16, the hyperesthesia therapeutic probe 430 includes a transducer part 430*a* and a wedge-shaped defect portion pad 430*b*. In the transducer part 430*a*, a plurality of flat-plate transducers 434 are connected in parallel. Each of the flat-plate transducers 434 includes an ultrasonic transducer constituted by: a piezoelectric element 432; a plate electrode 431 located at one side of the piezoelectric element 432; and a plate electrode 433 located at the other side of the piezoelectric element 432. A metal thin film 435 is provided in front of the transducer part 430*a* in the direction of propagation of ultrasound. The metal thin film 435 is made of, for example, stainless used steel (SUS), and has a thickness of, for example, about 0.3 mm in a case where the frequency of the ultrasound is 1 MHz, for example. The configuration of the manipulation section 160 is the same as that of the first embodiment described above.

The wedge-shaped defect portion pad 430*b* is formed by modeling an impression of a wedge-shaped defect portion from which enamel is removed. The wedge-shaped defect portion pad 430*b* is made of, for example, an elastic material such as silicone or a polymer resin, and is formed by pushing silicone rubber or the like against a wedge-shaped defect portion of a hyperesthesia patient where hyperesthesia occurs to model an impression. The wedge-shaped defect portion pad 430*b* includes a fluid inlet 436 and a fluid outlet 437.

The frequency of ultrasound is not specifically limited as long as cavitation occurs to allow a drug to permeate the wedge-shaped defect portion. For example, the frequency of ultrasound is 100 KHz to 10 MHz, preferably 800 KHz to 2 MHz, and particularly preferably about 1 MHz.

The intensity of ultrasound is not specifically limited as long as cavitation occurs in a preferable manner with dental tissue being not damaged. The intensity of ultrasound is 1-30 W/cm$^2$, for example, and preferably 10-25 W/cm$^2$, and particularly preferably about 20 W/cm$^2$.

A drug for use in hyperesthesia therapy is delivered in a mixed state with nanobubbles. The drug is not specifically limited. Examples of the drug include oxalic acid, a diamine silver fluoride product, copal resin, sodium fluoride, zinc chloride, a water-soluble aluminium compound, water-soluble calcium, BMPs, bFGF, and a mixture of one or more of these substances.

Figure 17A:
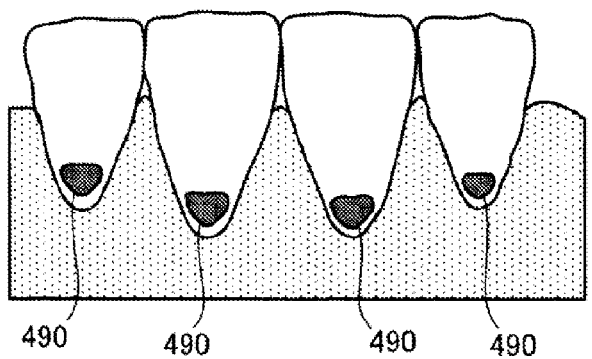
FIG. 17A is an illustration of wedge-shaped defect portions.
Figure 17B:
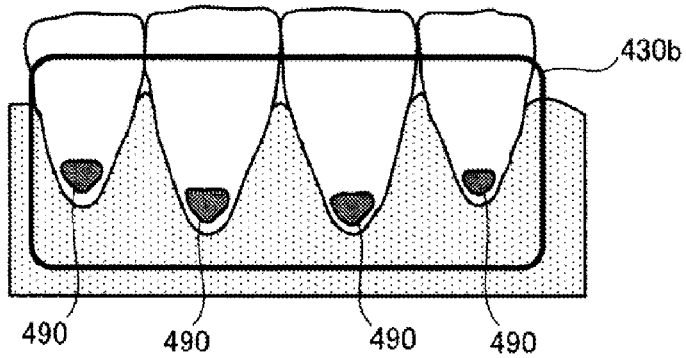
FIG. 17B is a view showing formation of a wedge-shaped defect portion pad by modeling an impression.
Figure 17C:
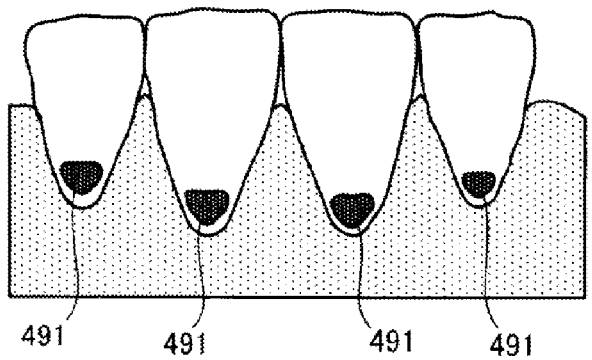
FIG. 17C is an illustration of a state in which the wedge-shaped defect portions are embrocated with a drug mixture and an ultrasonic conduction gel.
Figure 17D:
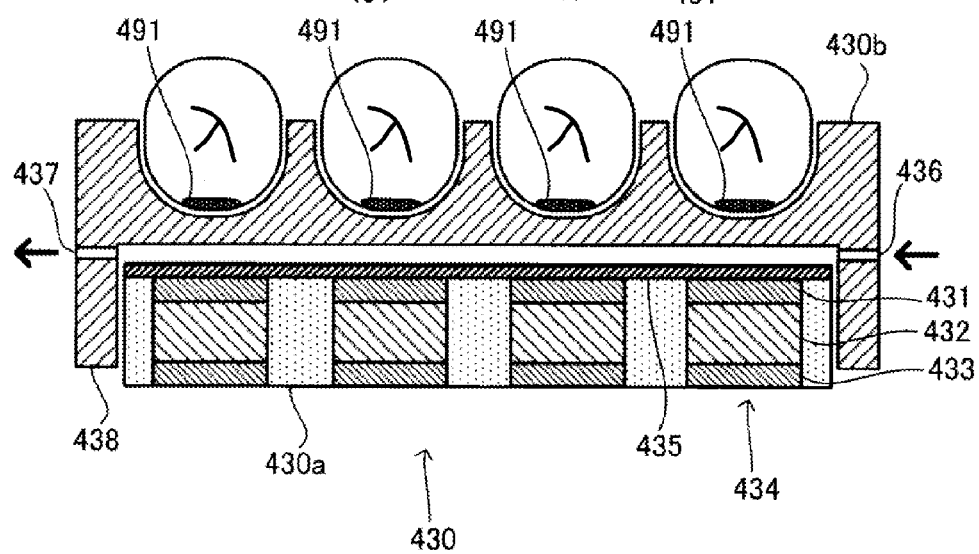
FIG. 17D is an illustration of a treatment of the wedge-shaped defect portions.

A mode of use of a dental ultrasonic drug delivery system 900 of this embodiment will now be described. FIGS. 17A-17D are views showing processes in which a treatment of wedge-shaped defect portions 490 is conducted by pushing the hyperesthesia therapeutic probe 430 of the dental ultrasonic drug delivery system 900 of this embodiment against the wedge-shaped defect portions 490 of a hyperesthesia patient which are a target of treatment. FIG. 17A is an illustration of the wedge-shaped defect portions 490. FIG. 17B is a view showing formation of the wedge-shaped defect portion pad 430*b*. FIG. 17C is an illustration of a state in which the wedge-shaped defect portions 490 are embrocated with a drug mixture and an ultrasonic conduction gel. FIG. 17D is an illustration of a treatment of the wedge-shaped defect portions 490.

The surface of a tooth is covered with enamel, which blocks external stimuli. However, as illustrated in FIG. 17A, when a periodontal disease causes gums to recede so that portions where enamel has been removed are exposed, wedge-shaped defect portions 490 are created, where dental pulp is directly stimulated through dentin tubules to cause hyperesthesia.

Next, as illustrated in FIG. 17B, an elastic material such as silicone is pushed against the wedge-shaped defect portions 490, thereby forming a wedge-shaped defect portion pad 430*b*.

Then, as illustrated in FIG. 17C, the wedge-shaped defect portions 490 are embrocated with the above-described drug mixture which is a mixture of a drug and nanobubbles and an ultrasonic conduction gel 491. The ultrasonic conduction gel 491 is a water-soluble gel having a high ultrasonic conductivity in a wide frequency range. The ultrasonic conduction gel 491 may not be applied.

Thereafter, as illustrated in FIG. 17D, with the transducer part 430*a* being fitted in the wedge-shaped defect portion pad 430*b*, the hyperesthesia therapeutic probe 430 is pushed against the wedge-shaped defect portions 490, and in the same manner as in the first embodiment, ultrasound is caused to propagate through the wedge-shaped defect portion pad 430*b* by manipulating the manipulation section 160. In this process, as indicated by the arrows in FIG. 17D, a liquid such as water is caused to flow from the fluid inlet 436 and be discharged from the fluid outlet 437. In this manner, even if a gap were present between the transducer part 430*a* and the wedge-shaped defect portion pad 430*b*, a flow of the liquid would eliminate the gap, resulting in continuous propagation of the ultrasound. Then, when the ultrasound reaches the wedge-shaped defect portions 490, cavitation occurs and destroys nanobubbles. The shock of the destruction allows the drug to reach deep areas of the dentin tubules. In the case of hyperesthesia, it is sometimes difficult to determine a tooth suffering from hyperesthesia. In this embodiment, however, the use of the wedge-shaped defect portion pad 430b for allowing ultrasound to propagate a plurality of teeth ensures an easy therapy of hyperesthesia.

In the same manner as in the first embodiment, the hyperesthesia therapeutic probe 430 is detachably fixed to the probe body 150 with a fixing screw 151 interposed therebetween. Accordingly, the root canal insertion probe 100 of the first embodiment can be replaced with the periodontal disease therapeutic probe 131 of this embodiment. The hyperesthesia therapeutic probe 430 may be integrated with the probe body 150.

(Sixth Embodiment)

Unlike the first through fifth embodiments, in a sixth embodiment, the frequency of ultrasound to be supplied to each of ultrasonic transducers of an apical area irradiation part 110 and a lateral branch irradiation part 120 varies at random.

The sterilization efficiency of a root canal 200 varies depending on the frequency of ultrasound. This is because minute individual differences in biological structure of, for example, cells and bacteria, factors (e.g., type, concentration, and amount) derived from drugs, and factors (e.g., shape and location) of transducers, for example, are related to one another in a complex manner.

In this embodiment, since the frequency of ultrasound to be supplied to each ultrasonic transducer varies at random, each ultrasonic vibration has a frequency component in a very wide range. Accordingly, even when conditions for administration of a drug differs among individuals, ultrasonic vibration includes a frequency component which can provide the maximum sterilization effect. In this manner, sterilization can be achieved at high efficiency independently of differences in conditions for administration of a drug.

Figure 18:
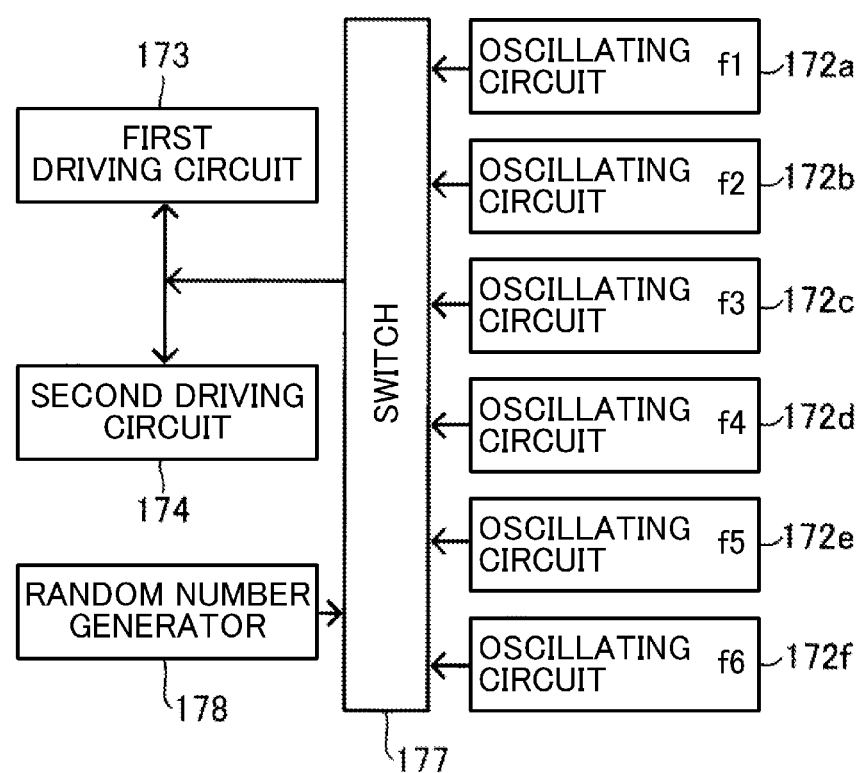
FIG. 18 is a diagram illustrating a configuration for random frequency generation.

FIG. 18 is a diagram illustrating a configuration for random frequency generation according to this embodiment. As illustrated in FIG. 18, a plurality of oscillating circuits 172a-172f respectively oscillating at frequencies f1-f6 in different ultrasonic frequency ranges. Outputs from the oscillating circuits 172a-172f are supplied to a switch 177.

The switch 177 is connected to a random number generator 178. One of the outputs from the oscillating circuits 172a-172f is selected depending on a random number generated by the random number generator 178, and is supplied to, for example, the first driving circuit 173 and the second driving circuit 174 of the first embodiment.

The random number generator 177 generates random numbers from "1" to "6." For example, when "4" is generated, the output of the frequency f4 from the oscillating circuit 172d is supplied. When "6" is generated, the output of the frequency f6 from the oscillating circuit 172f is supplied. In this manner, the frequency of ultrasound to be supplied to each ultrasonic transducer varies at random.

In this embodiment, the six frequencies f1-f6 are provided as frequencies in the ultrasonic frequency ranges. However, the present disclosure is not limited to this example, and the number of frequencies may be set at 3, 4, 5, or 7, for example.

(Seventh Embodiment)

Figure 19A:
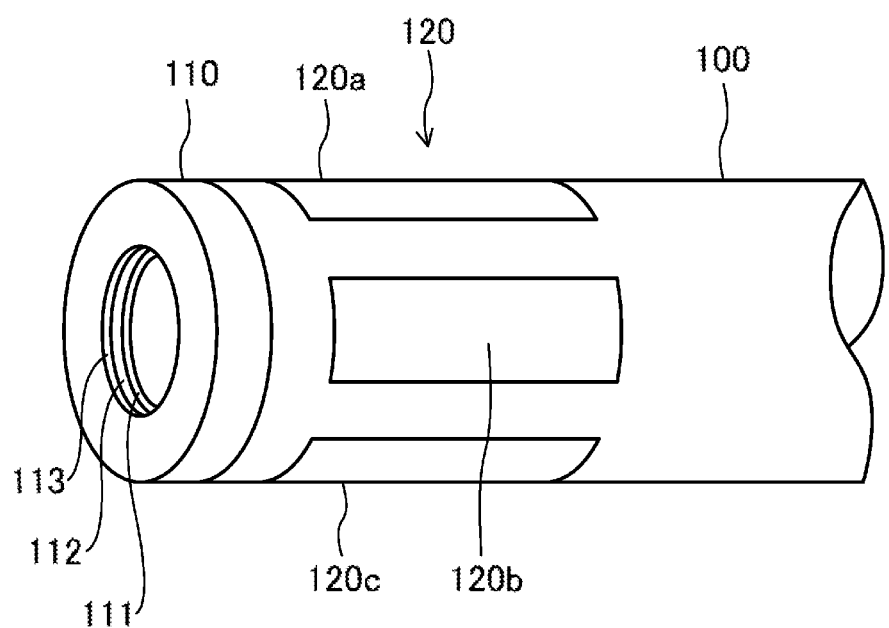
FIG. 19A is an outline view illustrating a configuration in which a plurality of lateral branch irradiation parts are provided on the circumference of a root canal insertion probe.
Figure 19B:
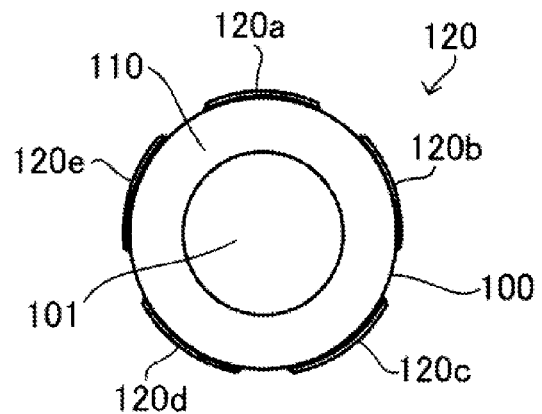
FIG. 19B is a front view illustrating a configuration in which the plurality of lateral branch irradiation parts are provided on the circumference of the root canal insertion probe, when viewed from the distal end of the probe.

Unlike the first embodiment, in a seventh embodiment, a plurality of lateral branch irradiation parts 120 are arranged at regular intervals on the circumference of a root canal insertion probe 100. FIGS. 19A and 19B are views illustrating a configuration in which a plurality of lateral branch irradiation parts 120a-120e are provided on a root canal insertion probe 100. FIG. 19A is an outline view, and FIG. 19B is a front view when viewed from the distal end of the probe.

As illustrated in FIGS. 19A and 19B, the lateral branch irradiation parts 120a-120e are arranged side by side at regular intervals in the circumferential direction on the circumference of the root canal insertion probe 100. Unlike the first embodiment, this arrangement allows the ultrasonic transducers of the lateral branch irradiation parts 120a-120e to be individually controlled to supply different frequencies.

(Eighth Embodiment)

Figure 20:
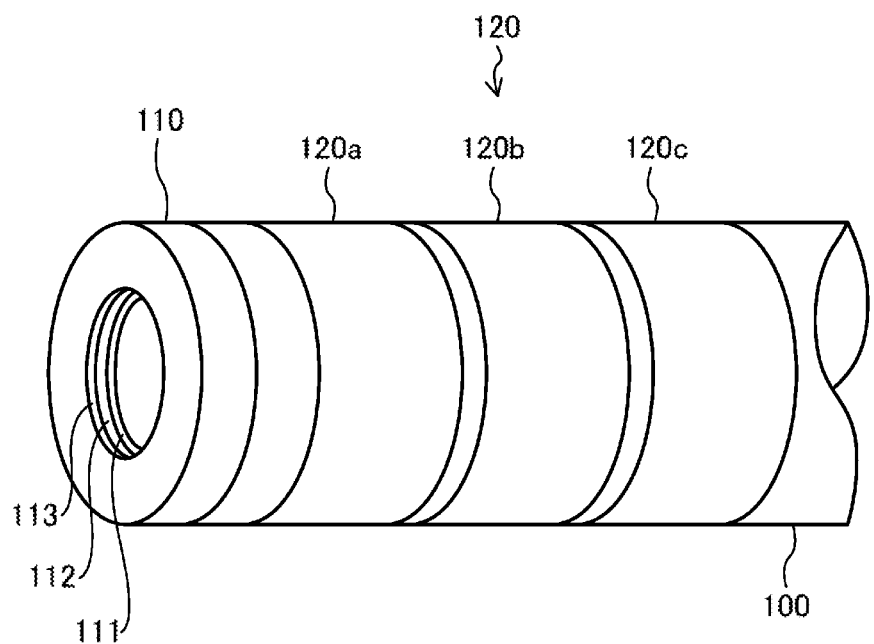
FIG. 20 is a view illustrating a configuration in which a plurality of lateral branch irradiation parts is arranged side by side along the axis of a root canal insertion probe.

Unlike the first embodiment, in an eighth embodiment, a plurality of lateral branch irradiation parts 120 are arranged side by side along the axis of a root canal insertion probe 100. FIG. 20 is a view illustrating a configuration in which a plurality of lateral branch irradiation parts 120a-120c are arranged side by side along the axis of the root canal insertion probe 100.

As illustrated in FIG. 20, the lateral branch irradiation parts 120a-120c are arranged side by side at regular intervals along the axis of the root canal insertion probe 100. This arrangement of the lateral branch irradiation parts 120a-120c along the axis of the root canal insertion probe 100 enables a wide range of a root canal 200 to be irradiated with ultrasound, thereby enlarging an area where cavitation occurs in the root canal 200.

The dental ultrasonic drug delivery systems of the foregoing embodiments are applicable not only to humans but also any other type of animals including Canidae animals, Felidae animals, Equidae animals, Bovidae animals, Suidae animals, and Leporidae animals. The American Veterinary Dental Society reports that 70% of cats and 80% of dogs have some form of gingival disease before the age of three years. According to the present disclosure, oral health problems in animals are significantly improved.

EXAMPLES

Specific examples of the present disclosure will be described hereinafter. The examples below are merely examples of the present disclosure, and do not limit the invention.

First Example

In-vitro Test for Drug Permeation in Root Canal Using Ultrasound and Nanobubbles After an extracted canine tooth had been subjected to access cavity preparation and root canal enlargement (to #60) by common methods, a smear layer was removed with a Smear Clean (Nippon Shika Yakuhin Co., Ltd.), and the tooth was refrigerated in a saline solution until being used in an experiment. Then, the inside of the root canal was sufficiently dried with a cotton plug. Thereafter, to prevent a drug solution from leaking from the root canal, an apical area was filled with a Unifast III (GC Corporation). Subsequently, nanobubbles were diluted with a saline solution such that the concentration of the nanobubbles is 5% or 10% (where the bubble concentration will be expressed in terms of vol % hereinafter), thereby preparing a drug solution containing 4.5 mg/ml tetracycline (SIGMA088K0680). The 5% nanobubbles herein mean that the concentration of the nanobubbles is $6\times10^8$/ml. The 10% nanobubbles herein mean that the concentration of the nanobubbles is $1.2\times10^9$/ml. Since even a small amount of deposited tetracycline produces fluorescence when irradiated with ultraviolet radiation, a deposition site can be easily detected with a fluorescence microscope. As a control, microbubbles (Optison (Molecular Biosystems Inc., San Diego)) were used, and a 5% or 10% drug solution was used. The 5% microbubbles herein mean that the concentration of the microbubbles is $6\times10^8$/ml. The 10% microbubbles herein mean that the concentration of the microbubbles is $1.2\times10^9$/ml. Then, 20 µl of the drug solution was applied into the root canal, and using an ultrasound generator (SonoPore KTAC-4000), an ultrasonic device with a diameter of 1 mm of a detachable irradiation tube propagation type probe (i.e., an applicator type in which a Langevin transducer is provided inside a probe body) was inserted into the root canal, and the device was operated. Operating conditions were that the voltage was 30 V (0.13-0.20 W indicated by a meter) or 31 V, the frequency was 1.186 MHz, the burst rate was 18.8 Hz, the pulse-duty ratio was 50%, and the application time was 120 seconds. After a lapse of the application time, the dilution solution was sufficiently removed with a cotton plug, and then a section with a thickness of 150 µm was prepared with a saw microtome (Leica SP1600), and a microscopic examination was performed with a stereomicroscope under ultraviolet irradiation. The degree of delivery of the drug into dentin tubules was observed based on fluorescence reaction.

Figure 21A:
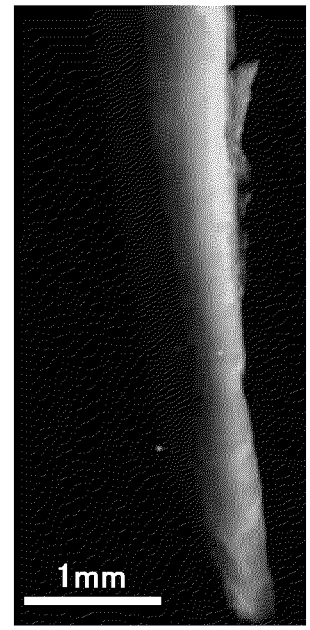
FIG. 21A is a micrograph showing the degree of delivery of a drug with a bubble concentration of 5% to dentin tubules in a case where ultrasound is applied at a voltage of 30 V with the use of nanobubbles.
Figure 21B:
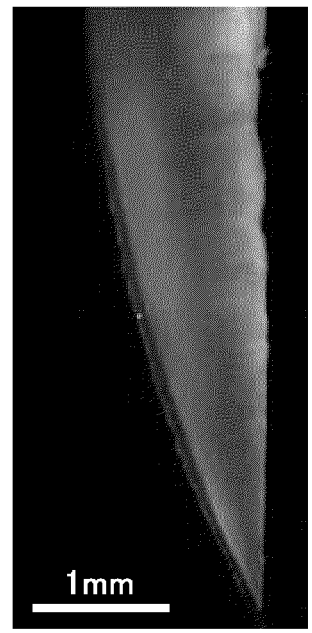
FIG. 21B is a micrograph showing the degree of delivery of a drug with a bubble concentration of 5% to dentin tubules in a case where ultrasound is applied at a voltage of 31 V with the use of nanobubbles.
Figure 21C:
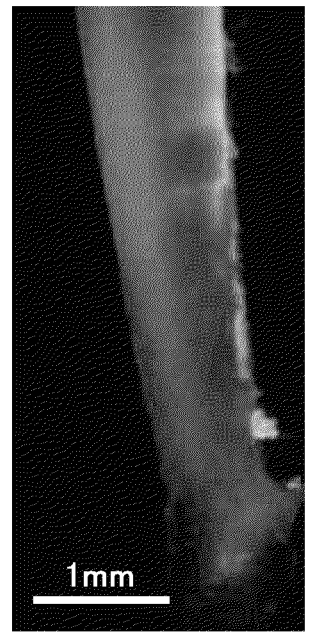
FIG. 21C is a micrograph showing the degree of delivery of a drug with a bubble concentration of 5% to dentin tubules in a case where no ultrasound is applied with the use of nanobubbles.
Figure 21D:
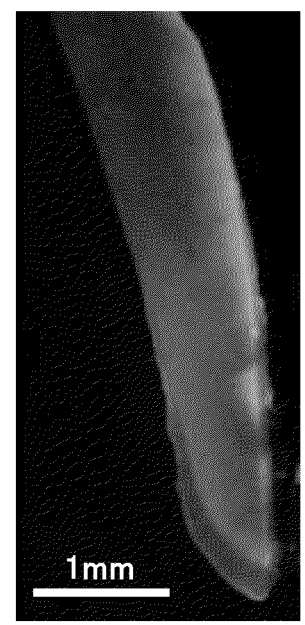
FIG. 21D is a micrograph showing the degree of delivery of a drug with a bubble concentration of 5% to dentin tubules in a case where ultrasound is applied at a voltage of 30 V with the use of microbubbles.
Figure 21E:
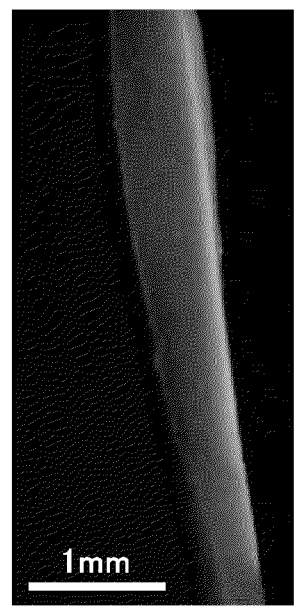
FIG. 21E is a micrograph showing the degree of delivery of a drug with a bubble concentration of 5% to dentin tubules in a case where no ultrasound is applied with the use of microbubbles.

FIGS. 21A-21E are photographs showing the degrees of delivery of a drug with a bubble concentration of 5% to dentin tubules. FIG. 21A is a micrograph at a voltage of 30 V with the use of nanobubbles. FIG. 21B is a micrograph at a voltage of 31 V with the use of nanobubbles. FIG. 21C is a micrograph without ultrasonic irradiation with the use of nanobubbles. FIG. 21D is a micrograph at a voltage of 30 V with the use of microbubbles. FIG. 21E is a micrograph without ultrasonic irradiation with the use of microbubbles.

As shown in FIG. 21A, in a case where ultrasound was applied with the use of nanobubbles, the degree of delivery of the drug to dentin tubules was high. However, as shown in FIG. 21C, in a case where no ultrasound was applied, the degree of delivery of the drug to dentin tubules was insufficient even with the use of nanobubbles. As shown in FIG. 21B, in a case where ultrasound was applied at 31 V, the ultrasonic energy was excessively high, resulting in that the degree of delivery of the drug to dentin tubules was insufficient. As shown in FIG. 21D, in a case where microbubbles were used, the degree of delivery of the drug to dentin tubules was insufficient even with irradiation of ultrasound. As shown in FIG. 21E, in a case where microbubbles were used and ultrasound was not applied, the degree of delivery of the drug to dentin tubules was insufficient.

Figure 22A:
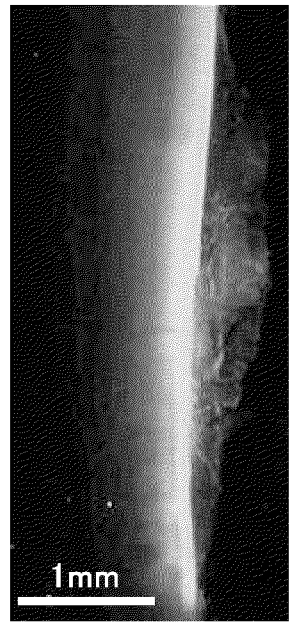
FIG. 22A is a micrograph showing the degree of delivery of a drug with a bubble concentration of 10% to dentin tubules in a case where ultrasound is applied at a voltage of 30 V with the use of nanobubbles.
Figure 22B:
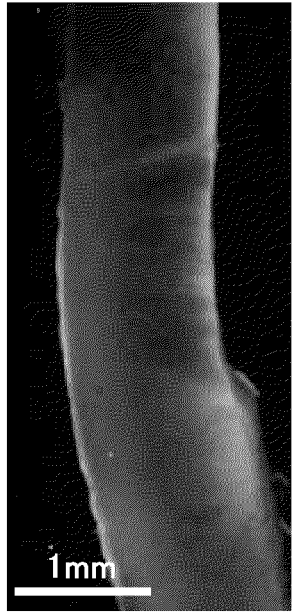
FIG. 22B is a micrograph showing the degree of delivery of a drug with a bubble concentration of 10% to dentin tubules in a case where ultrasound is applied at a voltage of 31 V with the use of nanobubbles.
Figure 22C:
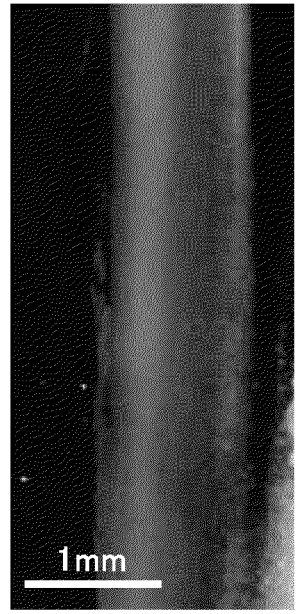
FIG. 22C is a micrograph showing the degree of delivery of a drug with a bubble concentration of 10% to dentin tubules in a case where no ultrasound is applied with the use of nanobubbles.
Figure 22D:
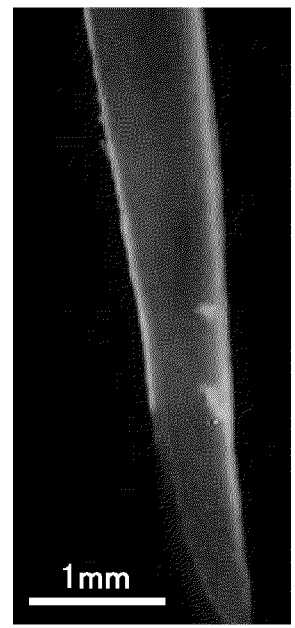
FIG. 22D is a micrograph showing the degree of delivery of a drug with a bubble concentration of 10% to dentin tubules in a case where ultrasound is applied at a voltage of 30 V with the use of microbubbles.
Figure 22E:
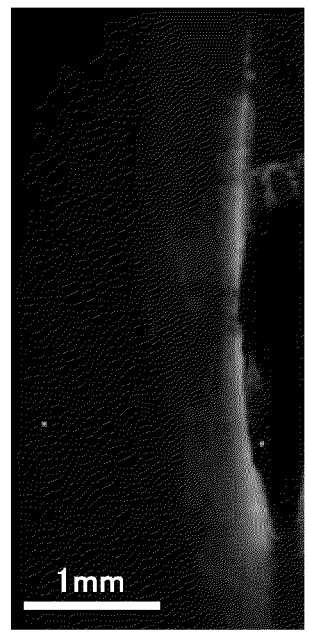
FIG. 22E is a micrograph showing the degree of delivery of a drug with a bubble concentration of 10% to dentin tubules in a case where no ultrasound is applied with the use of microbubbles.

FIGS. 22A-22E are photographs showing the degrees of delivery of a drug with a bubble concentration of 10% to dentin tubules. FIG. 22A is a micrograph at a voltage of 30 V with the use of nanobubbles. FIG. 22B is a micrograph at a voltage of 31 V with the use of nanobubbles. FIG. 22C is a micrograph without ultrasonic irradiation with the use of nanobubbles. FIG. 22D is a micrograph at a voltage of 30 V with the use of microbubbles. FIG. 22E is a micrograph without ultrasonic irradiation with the use of microbubbles.

As shown in FIG. 22A, in a case where ultrasound was applied with the use of nanobubbles, the degree of delivery of the drug to dentin tubules was high. However, as shown in FIG. 22C, in a case where no ultrasound was applied, the degree of delivery of the drug to dentin tubules was insufficient even with the use of nanobubbles. As shown in FIG. 22B, in a case where ultrasound was applied at 31 V, the ultrasonic energy was excessively high, resulting in that the degree of delivery of the drug to dentin tubules was insufficient. As shown in FIG. 22D, in a case where microbubbles were used, the degree of delivery of the drug to dentin tubules was insufficient even with irradiation of ultrasound. As shown in FIG. 22E, in a case where microbubbles were used and ultrasound was not applied, the degree of delivery of the drug to dentin tubules was insufficient.

As shown in FIGS. 21A and 22A, the degree of delivery of the drug to dentin tubules was higher in the case of 10% nanobubbles than in the case of 5% nanobubbles.

The foregoing experiment shows that the drug more significantly permeates in both the cases of concentrations of 5% and 10% with the use of nanobubbles than with the use of microbubbles. The 10% nanobubbles show superior permeation to that of the 5% nanobubbles, and both of the 5% and 10% nanobubbles exhibited the maximum degree of drug delivery at 30 V.

Second Example

Destruction Test of Nanobubbles and Microbubbles

An acrylic artificial root canal model was subjected to root canal enlargement to #60, and each of 10% microbubbles and 10% nanobubbles were injected into a root canal. Then, immediately after ultrasonic irradiation for 120 seconds with the voltage changed to 0, 30, 60, and 90 V, microscopy was conducted with a Dark-light Illuminator (NEPA GENE, Co., Ltd.) to evaluate the degree of destruction of the bubbles.

Figure 23A:
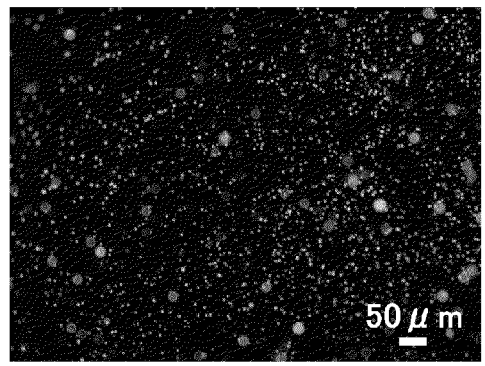
FIG. 23A is a photograph showing the degree of destruction of microbubbles by irradiation of a root canal insertion probe at a voltage of 0 V for 120 seconds, observed with a Dark-light Illuminator.
Figure 23B:
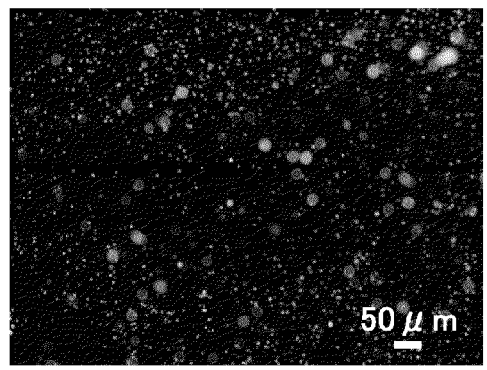
FIG. 23B is a photograph showing the degree of destruction of microbubbles by irradiation of a root canal insertion probe at a voltage of 30 V for 120 seconds, observed with a Dark-light Illuminator.
Figure 23C:
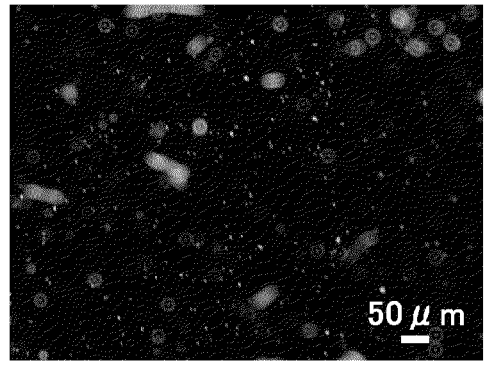
FIG. 23C is a photograph showing the degree of destruction of microbubbles by irradiation of a root canal insertion probe at a voltage of 60 V for 120 seconds, observed with a Dark-light Illuminator.
Figure 23D:
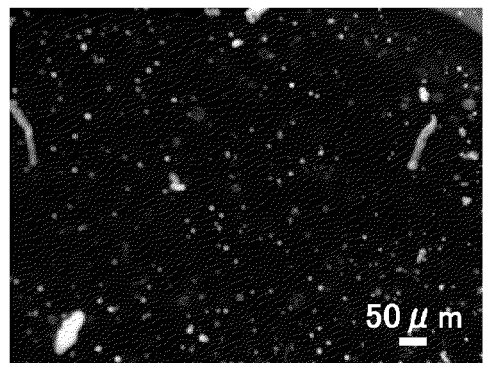
FIG. 23D is a photograph showing the degree of destruction of microbubbles by irradiation of a root canal insertion probe at a voltage of 90 V for 120 seconds, observed with a Dark-light Illuminator.
Figure 23E:
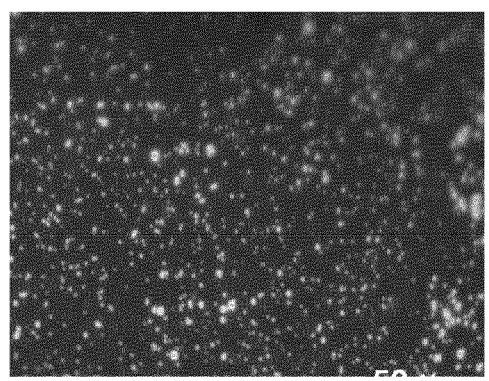
FIG. 23E is a photograph showing the degree of destruction of nanobubbles by irradiation of a root canal insertion probe at a voltage of 0 V for 120 seconds, observed with a Dark-light Illuminator.
Figure 23F:
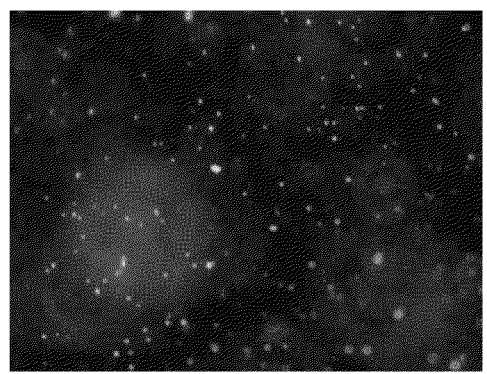
FIG. 23F is a photograph showing the degree of destruction of nanobubbles by irradiation of a root canal insertion probe at a voltage of 30 V for 120 seconds, observed with a Dark-light Illuminator.

FIGS. 23A-23F are photographs showing the degrees of destruction of microbubbles or nanobubbles by irradiation for 120 seconds with changes of the voltage with a root canal insertion probe, and observed with a Dark-light Illuminator. FIG. 23A shows a case where microbubbles were destroyed at a voltage of 0 V. FIG. 23B shows a case where microbubbles were destroyed at a voltage of 30 V (0.13-0.20 W indicated by a meter). FIG. 23C shows a case where microbubbles were destroyed at a voltage of 60 V (1.09 W indicated by a meter). FIG. 23D shows a case where microbubbles were destroyed at a voltage of 90 V (1.26-1.33 W indicated by a meter). FIG. 23E shows a case where nanobubbles were destroyed at a voltage of 0 V. FIG. 23F shows a case where nanobubbles were destroyed at a voltage of 30 V.

As shown in FIG. 23A-23D, when 10% microbubbles were irradiated with ultrasound for 120 seconds, the microbubbles started to be destroyed rapidly from 60 V. As shown in FIGS. 23E and 23F, when 10% nanobubbles were irradiated with ultrasound for 120 seconds, power started to be generated rapidly from 30 V, nanobubbles were slowly destroyed, and 95% or more of nanobubbles disappeared in 120 seconds. On the other hand, at 40 V, nanobubbles were more rapidly destroyed, and the nanobubbles disappeared in about 80 seconds. From the foregoing results, the voltage at which cavitation of nanobubbles occurs is lower than the voltage at which cavitation of microbubbles occurs. Thus, drug delivery using nanobubbles is advantageous in terms of not only electrical energy saving but also safety.

Third Example

In vitro Tubule Sterilization Test Using Ultrasound and Nanobubbles

In the same manner as in the above examples, a root canal was enlarged and a smear layer was removed. Then, the inside of the root canal was sufficiently dried with a cotton plug, and an apical area was filled with a Unifast III (GC Corporation). Thereafter, 5 µl of a bacterial culture (a brain heart infusion (BHI) broth, Nissui Pharmaceuticals Co., Ltd., containing kanamycin) in which kanamycin-resistant *enterococcus faecalis* (*lactococcus*) subjected to gene transfer of pEGFP-C1 (clontech) was cultured was injected into each root canal. Subsequently, the root canal was temporarily sealed with Hyseali (Shofu Inc.), and cultivation was conducted at 36.8° C. under aerobic and wet conditions with an incubator (Yamato Scientific Co., Ltd., IC602) for six days, thereby forming a pseudo infected root canal. After removal of the temporary seal, the root canal was irrigated with 3 ml of a saline solution, and dried with a sterilized paper point #55 (Morita Corporation). Then, a drug solution was prepared under conditions shown in Table 1 below, and 7 µl of the drug solution was injected into the root canal.

TABLE 1

| | nanobubbles (undiluted) (microliter) | ampicillin (0.5 mg/ml) (microliter) | saline solution (microliter) | ultrasound | infection |
|---|---|---|---|---|---|
| a | 0 | 0 | 20 | — | not observed |
| b | 0 | 0 | 20 | — | observed |
| c | 2 | 2 | 16 | +30 V | not observed |
| d | 0 | 2 | 18 | — | observed |
| e | 2 | 0 | 18 | +30 V | observed |
| f | microbubbles | 2 | 16 | +60 V | observed |

In the same manner as in the above examples, an ultrasonic device with a diameter of 1 mm of a detachable irradiation tube propagation type probe (i.e., an applicator type in which a Langevin transducer is provided inside a probe body) was inserted into the root canal, and the device was operated. Operating conditions with nanobubbles were that the voltage was 30 V (0.13-0.20 W indicated by a meter), the frequency was 1.186 MHz, the burst rate was 18.8 Hz, the pulse-duty ratio was 50%, and the application time was 120 seconds. As microbubbles, 2 µl of 10% microbubbles were used. Operating conditions with microbubbles were that the voltage was 60 V (1.09 W indicated by a meter), the frequency was 1.186 MHz, the burst rate was 18.8 Hz, the pulse-duty ratio was 50%, and the application time was 120 seconds. The root canal was dried with a paper point and temporarily sealed with a Caviton. Then, cultivation was conducted under aerobic and wet conditions for 48 hours. After 48 hours, a section with a thickness of 150 µm was prepared with a saw microtome (Leica SP1600), and the state of killing of bacteria was morphologically observed with a confocal laser scanning microscope.

Figure 24A:
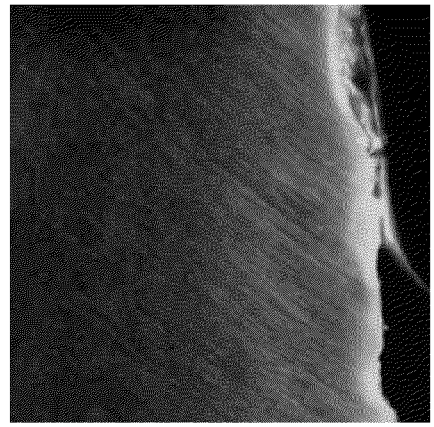
FIG. 24A is a photograph showing a root canal of an extracted canine tooth not infected by *enterococcus faecalis* (*lactococcus*).
Figure 24B:
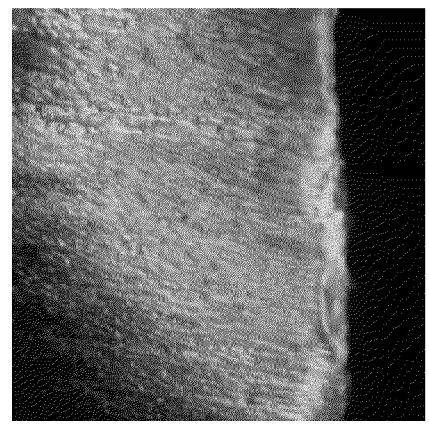
FIG. 24B is a photograph showing a root canal of an extracted canine tooth artificially infected by *enterococcus faecalis* (*lactococcus*) in vitro for 7 days.
Figure 24C:
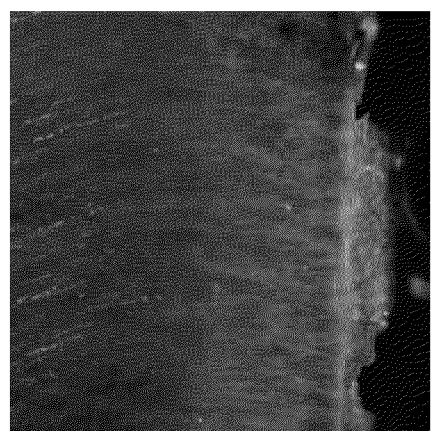
FIG. 24C is a photograph showing sterilization in which a root canal of an extracted canine tooth artificially infected by *enterococcus faecalis* (*lactococcus*) in vitro for 7 days was sterilized by drug delivery using ultrasound at 30 V and 10% nanobubbles, and showing the state on the second day after the use of ampicillin.
Figure 24D:
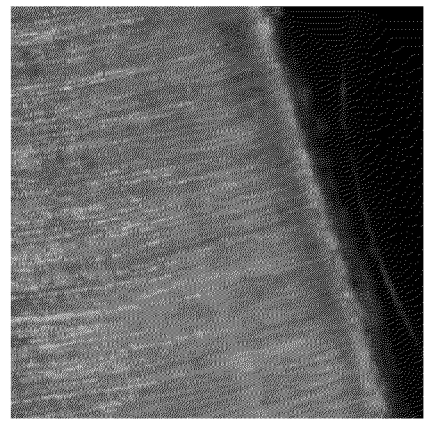
FIG. 24D is a photograph showing the state on the second day in which ampicillin was used for a root canal of an extracted canine tooth artificially infected by *enterococcus faecalis* (*lactococcus*) in vitro for 7 days.
Figure 24E:
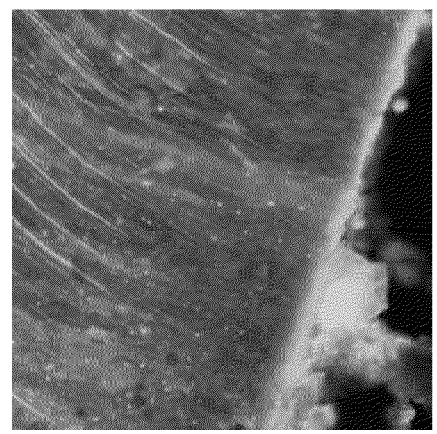
FIG. 24E is a photograph showing the state on the second day in which ultrasound at 30 V and 10% nanobubbles were used for a root canal of an extracted canine tooth artificially infected by *enterococcus faecalis* (*lactococcus*) in vitro for 7 days.
Figure 24F:
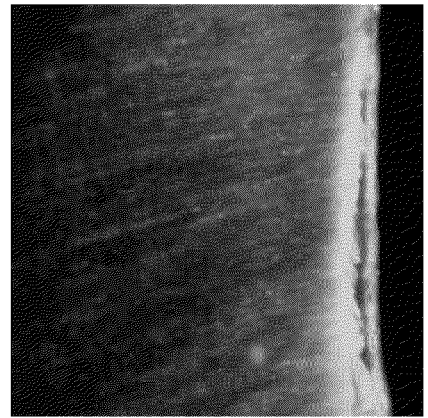
FIG. 24F is a photograph showing the state in which drug delivery using ultrasound at 60 V and 10% microbubbles was performed on a root canal of an extracted canine tooth artificially infected by *enterococcus faecalis* (*lactococcus*) in vitro for 7 days, and showing the state on the second day after the use of ampicillin.

FIGS. 24A-24F are photographs showing sterilization by drug delivery using ultrasound and bubbles after a root canal was artificially infected by *enterococcus faecalis* (*lactococcus*) in vitro for 7 days. FIG. 24A shows the case of no infection ("a" in Table 1). FIG. 24B shows the case of an untreated control ("b" in Table 1). FIG. 24C shows the state on the second day after the use of 10% nanobubbles, an ultrasonic voltage of 30 V, and ampicillin ("c" in Table 1). FIG. 24D shows the state on the second day after the use of only ampicillin ("d" in Table 1). FIG. 24E shows the state on the second day after the use of 10% nanobubbles and an ultrasonic voltage of 30 V ("e" in Table 1). FIG. 24F shows the state on the second day after the use of 10% microbubbles, an ultrasonic voltage of 60 V, and ampicillin ("f" in Table 1).

In the case of "b," i.e., a control in which none of ultrasound, nanobubbles, and ampicillin was delivered, bacteria invaded to a depth of about 100 µm in dentin tubules in the lateral wall of the root canal. On the other hand, in the case of "c" where ampicillin was delivered using 10% nanobubbles and ultrasound, no bacteria were observed in the lateral wall of the root canal. In the cases of "d" where only ampicillin was used and "e" where only nanobubbles and ultrasound were used, bacteria were not completely killed. In the case of "f" where ampicillin was delivered using 10% microbubbles and ultrasound, a larger number of bacteria remained than that in the case of "c."

In the same manner, an ultrasonic test was conducted in the following manner. After 48 hours from ultrasound delivery, a temporary seal was removed, 8 µl of a kanamycin-containing culture solution was added to the root canal, and then cultivation was conducted under aerobic and wet conditions for 24 hours. After the removal of the temporary seal, 10 µl of a culture solution was applied into the root canal, and the root canal model was left for 3 minutes. Thereafter, the culture solution was taken out, and diluted to 1/100, 1/1000, 1/10000, 1/100000, and 1/1000000 with a 100-fold dilution method. The each of the resultant culture solutions was plated on a kanamycin-containing BHI plate culture medium, and further cultured for 24 hours. For bacterial count, a diluted solution in which the number of bacteria (the number of colonies) was about 50-500 was selected, and the number of bacteria was counted. As a result, in the case of "c" where ampicillin was delivered using 10% nanobubbles and ultrasound, proliferation of bacteria was more significantly suppressed than in the cases of "d" using only ampicillin, "e" using only nanobubbles and ultrasound, and "f" in which ampicillin was delivered using 10% microbubbles and ultrasound.

Fourth Example

In vivo Tubule Sterilization Test Using Ultrasound and Nanobubbles

After a canine tooth had been subjected to access cavity preparation and root canal enlargement (to #60) in vivo by common methods, a smear layer was removed with a Smear Clean (Nippon Shika Yakuhin Co., Ltd.). Then, the inside of the root canal was sufficiently dried with a cotton plug. Thereafter, 10 µl of a bacterial culture (a brain heart infusion (BHI) broth, Nissui Pharmaceuticals Co., Ltd., containing kanamycin) in which kanamycin-resistant *enterococcus faecalis* (*lactococcus*) subjected to gene transfer of pEGFP-C1 (clontech) was cultured was injected into each root canal. Subsequently, the root canal was temporarily sealed with zinc phosphate cement. Then, after 7 days, the root canal was irrigated with 3 ml of a saline solution. Thereafter, 20 µl of a drug solution containing 10% nanobubbles and 50 µg/ml of ampicillin was applied into the root canal. Then, with an ultrasound generator (SonoPore KTAC-4000), an ultrasonic device with a diameter of 1 mm of a detachable irradiation tube propagation type probe (i.e., an applicator type in which a Langevin transducer is provided inside a probe body) was inserted into the root canal, and ultrasound was delivered at a voltage of 30 V, a frequency of 1.186 MHz, a burst rate of 18.8 Hz, a pulse-duty ratio of 50% for an application time of 120 seconds. After a lapse of the application time, a section with a thickness of 150 µm was prepared with a saw microtome (Leica SP1600), and observation was performed with a confocal laser scanning microscope.

Figure 25A:
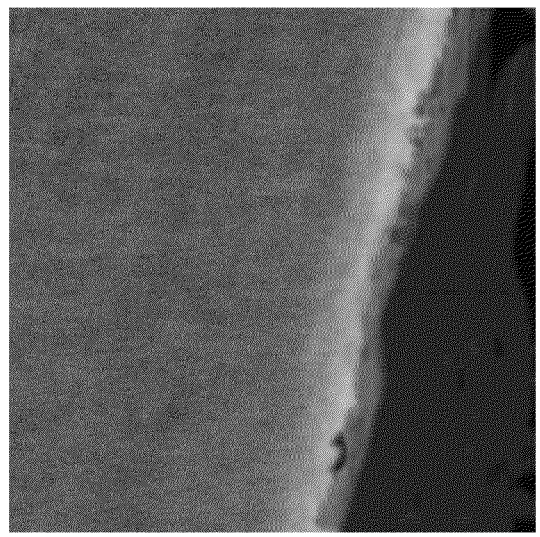
FIG. 25A is a photograph showing the state in which ampicillin delivery using ultrasound at 30 V and 10% nanobubbles was performed on a root canal of a canine tooth artificially infected by *enterococcus faecalis* (*lactococcus*) in vivo for 7 days.
Figure 25B:
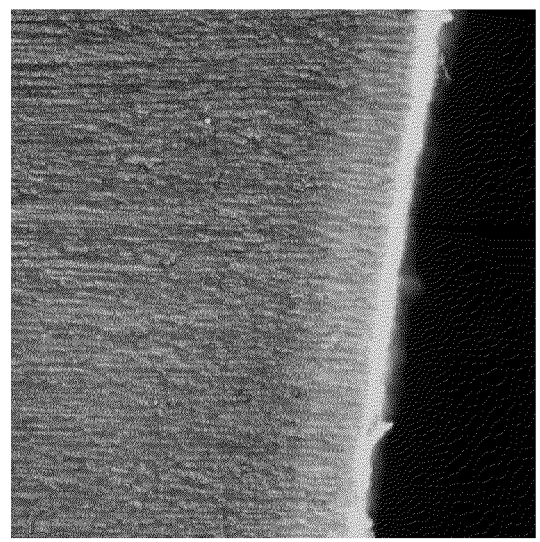
FIG. 25B is a photograph showing the state on the fourth day of the use of ampicillin for a root canal of a canine tooth artificially infected by *enterococcus faecalis* (*lactococcus*) in vivo for 7 days.
Figure 25C:
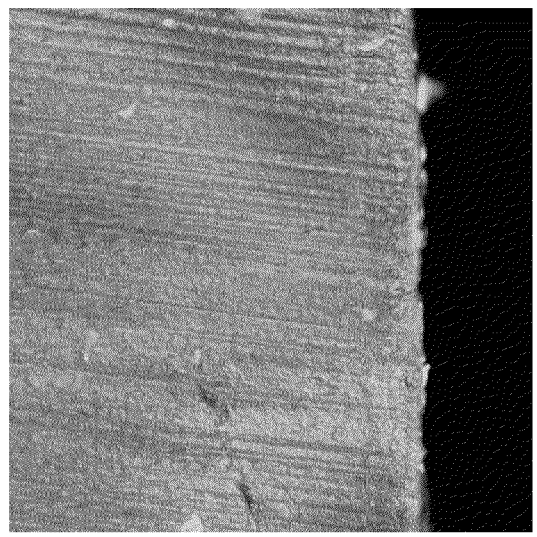
FIG. 25C is a photograph showing a root canal of a canine tooth artificially infected by *enterococcus faecalis* (*lactococcus*) in vivo for 7 days.

FIGS. 25A-25C are photographs showing sterilization by ampicillin drug delivery using ultrasound and bubbles after a root canal of a canine tooth was artificially infected by *enterococcus faecalis* (*lactococcus*) for 7 days. FIG. 25A shows the state on the fourth day after the use of 10% nanobubbles, ultrasound (at 30 V (0.13-0.20 W indicated by a meter)), and ampicillin. FIG. 25B shows the state on the fourth day after the use of only ampicillin FIG. 25C shows the case of an untreated control. As shown in FIG. 25C, in the untreated control in which none of ultrasound, nanobubbles, and ampicillin was delivered, bacteria invaded to a depth of about 100 μm in dentin tubules in the lateral wall of the root canal. On the other hand, as shown in FIG. 25A, in the tooth in which ampicillin was delivered using 10% nanobubbles and ultrasound, no bacteria were observed in the lateral wall of the root canal. As shown in FIG. 25B, in the case of using only ampicillin, bacteria were not completely killed.

Fifth Example

Particle Size Distribution Analysis of Nanobubbles and Microbubbles

Figure 26:
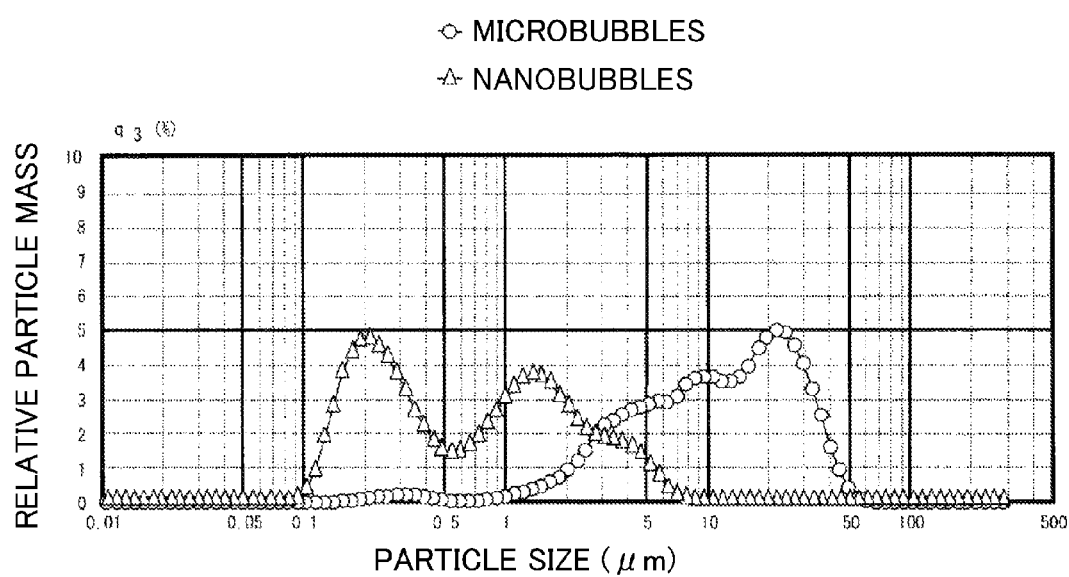
FIG. 26 is a graph showing particle size distributions of nanobubbles and microbubbles.

Particle size distributions of the nanobubbles used in the first through fourth examples and the microbubbles used in the first through third examples were analyzed with a Shimadzu nanoparticle size analyzer (SALD-7100, Shimadzu Corporation). FIG. 26 is a graph showing particle size distributions of nanobubbles and microbubbles. As shown in FIG. 26, the nanobubbles used in the first through fourth examples had particle size distributions mainly in the range from 100 nm to 500 nm. On the other hand, the nanobubbles used in the first through third examples had particle size distributions mainly in the range from 1 μm to 50 μm.

Sixth Example

In vitro Tubule Sterilization Test Using Dental Root Canal Irrigation Agent, Sodium Hypochlorite, and Nanobubbles Using ten extracted bovine teeth (anterior teeth), the apical area of each of the teeth was filled with photopolymerization type ionomer cement. Then, the inside of the root cavity was treated with 6% sodium hypochlorite, irrigated, and sterilized with an autoclave. Thereafter, the inside of the root canal was sufficiently irrigated with a sterilized saline solution, dried with a paper point, filled with an *E. Coli* saturated solution, and then cultured in a humidity bath at 37° C. for a night. Then, the *E. Coli* solution in the root canal was sucked with a paper point, and the root canal was filled with an irrigation solution and 1% or 0.1% sodium hypochlorite. Thereafter, 5% nanobubbles were injected into the root canal, and ultrasound was applied thereto at a voltage of 30 V, a frequency of 1.186 MHz, a burst rate of 18.8 Hz, and a pulse-duty ratio of 50% for 120 seconds. Subsequently, the root canal was sufficiently irrigated with a saline solution, and the tooth was left for one minute with a paper point inserted into the root canal. Then, the paper point was cultured. After 12 hours, the amount of bacteria was measured with an absorbance $OD_{600}$. Table 2 shows the results.

TABLE 2

| sodium hypochlorite | 5% nanobubbles | $OD_{600}$ value |
|---|---|---|
| 0 | − | 2.094 |
| 0 | + | 2.246 |
| 0.1 | − | 0.294 |
| 0.1 | − | 0.590 |
| 0.1 | + | 0 |
| 0.1 | + | 0.004 |
| 1.0 | − | 0 |
| 1.0 | − | 0 |
| 1.0 | + | 0 |
| 1.0 | + | 0 |

In the case of 1% sodium hypochlorite, a bactericidal effect was obtained irrespective of the presence of 5% nanobubbles. However, in the case of 0.1% sodium hypochlorite, the inside of the root canal was sterilized only in the presence of 5% nanobubbles.

Sodium hypochlorite used for irrigation root of the root canal has cytotoxicity, and when leaking into oral mucosal or leaking from an apical area to the outside, might damage oral mucosal gingivae or apical periodontal tissue. However, when used together with nanobubbles, sodium hypochlorite is expected to be effective even in a low concentration where cytotoxicity is low. Thus, the use of low-concentration sodium hypochlorite for root canal irrigation can sterilize the inside of the root canal with safety. Even if sodium hypochlorite leaks from an apical area to the outside, damage of apical periodontal tissue can be prevented.

In addition, even if a biofilm (i.e., a film of exopolysaccharide formed by bacteria where many types of bacteria firmly aggregate) is formed in a periapical lesion outside an apical foramen, only a drug which can enter this biofilm exhibits a sufficient bactericidal effect. For this reason, sodium hypochlorite in a relatively high concentration of, for example, 470-600 ppm is used. However, when this sodium hypochlorite leaks from an apical area to the outside, the sodium hypochlorite might damage apical periodontal tissue. However, when used together with nanobubbles, sodium hypochlorite is expected to be effective even in a low concentration where cytotoxicity is low. Thus, the use of low-concentration sodium hypochlorite can break the biofilm with safety to kill bacteria.

DESCRIPTION OF REFERENCE CHARACTERS 100 root canal insertion probe
101 aperture
102 hollow part
110 apical area irradiation part
111 inner electrode
112 piezoelectric element
113 outer electrode
120 lateral branch irradiation part
121 inner electrode
122 piezoelectric element
123 outer electrode
130 dental caries therapeutic probe
131 periodontal disease therapeutic probe
132 drug tube
140 connection unit
150 probe body
160 manipulation section
177 switch
178 random number generator
180 Langevin transducer
200 root canal 210 main root canal
220 lateral branch
230 apical area
240 cementum
241 alveolar bone
242 enamel
243 dentin
244 dental pulp
245 dental cervix mucosal epithelium
247 odontoblast
248 dentin tubule
249 periodontium
260 periapical lesion
270 dental caries portion
310 nanobubbles
311 bacteria
320 drug
410 trigger
411 drug storage part
430 hyperesthesia therapeutic probe
450 drug delivery tube
480 periodontal pocket
490 wedge-shaped defect portion
800 ultrasonic delivery device
900 dental ultrasonic drug delivery system

The invention claimed is:

1. A dental ultrasonic drug delivery system comprising:
a drug mixed with nanobubbles;
a dental therapeutic probe; and
an ultrasonic transducer configured to deliver ultrasonic energy from the dental therapeutic probe at a frequency in the range from 800 KHz to 2 MHz, both inclusive, wherein
the dental ultrasonic drug delivery system delivers the drug to a target,
the dental therapeutic probe includes a probe body and an introduction probe attached to the probe body and configured to be used for introducing the drug to the target,
the dental therapeutic probe is a hyperesthesia therapeutic probe, which includes a wedge-shaped defect portion pad formed by modeling an impression of a wedge-shaped defect portion of tooth enamel, the ultrasonic transducer configured to generate the ultrasonic energy, and a fluid path, which is located between the ultrasonic transducer and the wedge-shaped defect portion pad, and through which a fluid flows, the hyperesthesia therapeutic probe being configured to apply the ultrasonic energy to a hyperesthesia portion, and
the wedge-shaped defect portion pad comprises at least one depressed portion of which a cross-section perpendicular to a root canal direction is generally a semicircular recess.

2. The dental ultrasonic drug delivery system of claim 1, wherein the target is a wedge-shaped defect portion of enamel.

3. The dental ultrasonic drug delivery system of claim 1, wherein each of the nanobubbles has a diameter of 10 nm to 500 nm, both inclusive.

4. The dental ultrasonic drug delivery system of claim 1, wherein the drug includes at least one of oxalic acid, a diamine silver fluoride product, copal resin, sodium fluoride, zinc chloride, a water-soluble aluminum compound, water soluble calcium, BMPs, or bFGF.

* * * * *